(12) United States Patent
Weeks et al.

(10) Patent No.: US 7,812,224 B2
(45) Date of Patent: Oct. 12, 2010

(54) METHODS AND MATERIALS FOR MAKING AND USING TRANSGENIC DICAMBA-DEGRADING ORGANISMS

(75) Inventors: Donald P. Weeks, Lincoln, NE (US);
Xiao-Zhuo Wang, Chapel Hill, NC (US); Patricia L. Herman, Waverly, NE (US)

(73) Assignee: Board of Regents of University of Nebraska, Lincoln, NE (US)

( * ) Notice: Subject to any disclaimer, the term of this patent is extended or adjusted under 35 U.S.C. 154(b) by 372 days.

(21) Appl. No.: 10/330,662

(22) Filed: Dec. 27, 2002

(65) Prior Publication Data

US 2003/0115626 A1 Jun. 19, 2003

Related U.S. Application Data

(60) Division of application No. 09/797,238, filed on Feb. 28, 2001, now Pat. No. 7,105,724, which is a continuation-in-part of application No. 09/055,145, filed on Apr. 3, 1998, now Pat. No. 7,022,896.

(60) Provisional application No. 60/042,666, filed on Apr. 4, 1997, provisional application No. 60/042,941, filed on Apr. 4, 1997.

(51) Int. Cl.
*C12N 15/82* (2006.01)
*C12N 15/53* (2006.01)
(52) U.S. Cl. .................... 800/300; 435/419; 435/320.1; 536/23.2; 800/298
(58) Field of Classification Search ................ 800/300, 800/288; 435/320.1, 419, 252.3; 536/23.2, 536/23.7
See application file for complete search history.

(56) References Cited

U.S. PATENT DOCUMENTS

| | | | | |
|---|---|---|---|---|
| 4,816,403 | A | 3/1989 | Roy | 435/253.3 |
| 5,263,992 | A | 11/1993 | Guire | |
| 5,362,865 | A | 11/1994 | Austin | 536/24.1 |
| 5,445,962 | A * | 8/1995 | Atallah et al. | 435/252.1 |
| 5,545,818 | A | 8/1996 | McBride et al. | 800/205 |
| 5,563,328 | A | 10/1996 | Mitra et al. | 800/250 |
| 5,608,147 | A * | 3/1997 | Kaphammer | 800/294 |
| 5,656,422 | A | 8/1997 | Crawford et al. | 435/4 |
| 5,670,454 | A | 9/1997 | Grossmann et al. | 504/244 |
| 7,022,896 | B1 * | 4/2006 | Weeks et al. | 800/300 |

FOREIGN PATENT DOCUMENTS

| | | |
|---|---|---|
| CA | 2165036 | 6/1996 |
| DE | 19533682 | 3/1997 |
| FR | 2655048 | 5/1991 |
| WO | WO 93/09176 | 5/1993 |
| WO | WO 93/16176 | 8/1993 |
| WO | WO 96/36653 | 11/1996 |
| WO | WO 97/41228 | 6/1997 |
| WO | WO 98/45424 | 10/1998 |
| WO | WO 02/068607 | 9/2002 |

OTHER PUBLICATIONS

Donaldson et al 1991, Plant Physiology 96:669-674.*
Lazar et al 1988, Mol. Cell. Biol. 8:1247-1252.*
Hill et al 1998, Biochem. Biophys. Res. Comm. 244:573-577.*
Guo et al 2004, Proc. Natl. Acad. Sci. USA 101: 9205-9210.*
Cork et al, 1995, Advances in Applied Microbiology, 40: 289-321.*
Khalil et al 2000 Microbis 102: 183-191.*
Spencer et al 1992 Plant Molecular Biology 18: 201-210.*
Yang et al 1994, Analytical Biochemistry 219: 37-42.*
Yang et al 1994, Analytical Biochemistry 219: 37-42.*
Weeks et al 1994, Journal of Cellular Biochemistry, Suppl. 18a, p. 91, Abstract X1-127.*
Erickson et al 1993, Applied and Environmental Microbiology 59(11): 3858-3862.*
Ai-Khatib et al., 1992, *Weed Technology*, 6:57-61.
Baker, 1993, *Weed Technology*, 7:150-153.
Batie et al., *Chemistry and Biochemistry of Flavoenzymes*, vol. III, Chapter 18, pp. 543-556.
Batie et al., 1987, *J. Biol. Chem.*, 202(4):1510-1516.
Bernhardt et al., 1975, *Eur. J. Blochem.*, 57:241-256.
Cork et al., 1995, *Advances in Applied Microbiology*, 40:289-321.
Cork et al., 1991, *Advances in Applied Microbiology*, 36:1-67.
Crop Protection Reference, 11th Edition, pp. 1803-1821 (1995).
Dehmel et al., 1995, *Arch Microbiol*, 163:35-41.
Fogarty et al., *J. Inudstrial Microbiology*, 5:365-370 (1995).
Fukumori et al., 1993, *J. Biological Chemistry*, 268(82):24311-24317.
Harayama et al., 1992, *Ann. Rev. Microbial*, 46:565-601.
Jasieniuk et al., 1995, *Weed Science*, 43:192-195.
Koziel et al., *Plant Mol. Biol.*, 32:393-405 (1996).

(Continued)

*Primary Examiner*—David H Kruse
(74) *Attorney, Agent, or Firm*—Sheridan Ross PC

(57) ABSTRACT

The invention provides isolated and at least partially-purified dicamba-degrading enzymes, isolated DNA molecules coding for dicamba-degrading enzymes, DNA constructs coding for dicamba-degrading enzymes, transgenic host cells comprising DNA coding for dicamba-degrading enzymes, and transgenic plants and plant parts comprising one or more cells comprising DNA coding for dicamba-degrading enzymes. Expression of the dicamba-degrading enzymes results in the production of dicamba-degrading organisms, including dicamba-tolerant plants. The invention further provides a method of controlling weeds in a field containing the transgenic dicamba-tolerant plants of the invention and a method of decontaminating a material containing dicamba comprising applying an effective amount of a transgenic microorganism or dicamba-degrading enzyme(s) of the invention to the material. Finally, the invention provides a method of selecting transformed plants and plant cells based on dicamba tolerance and a method of selecting or screening transformed host cells, intact organisms and parts of organisms based on the fluorescence of 3,6-dichlorosalicylic acid produced as a result of dicamba degradation.

19 Claims, 3 Drawing Sheets

OTHER PUBLICATIONS

Krueger et al., *J. Agric. Food Chem.*, 39:1000-1003 (1991).
Krueger et al., 1989, *J. Agric. Food Chem.*, 37:534-538.
Le et al., *J. of Bacteriology*, 175(23):7707-7710 (1993).
Magnusson et al., 1987, *Weed-Science*, 35:846-852.
Markus et al., 1986, *J Biological Chem.*, 261(27):12883-12888.
Mason et al., 1992, *Ann. Rev. Microbiol.*, 46:277-305.
Meikle et al., 1995, Brighton Crop Protection Conference, *Weeds*, 5A-3:439-444.
Nakatsu et al., 1995, *Microbiology*, 141:485-495.
O'Keefe et al., 1991, *Biochemistry*, 30:447-455.
Peniuk et al., 1993, *Weed Research*, 33:431-440.
Romanov et al., 1994, *J. Bacteriology*, 176(11):3368-3374.
Rosche et al., 1995, *Biochimica of Biophysica Acta*, 1252:177-179.
Sarpe et al., 1987, *Fragmenta herbologica Jugoslavica*, 16(1-2):299-305.
Schroeder et al., 1989, *Weed Technology*, 3:67-71.
Wang et al., 1997, *Applied and Environmental Microbiology*, 63(4):1623-1626.
Wang, "Characterization of Cellular and Enzymatic Degradation of Dicamba by *Pseudomonas maltophilia*, Strain DI-6," Thesis, University of Nebraska, (Thesis dated Aug. 1996).
Wicks et al., 1993, *Weed Science*, 41:225-231.
Yang et al., 1994, *Analytical Biochemistry*, 219:37-42.
Yuan et al., *Plant Biotechnology*, 8:227-233 (1997).
Wang et al., "A three component O-demethylase enzyme from *Pseudomonas maltophilia* catalyzes the first step in degradation of the herbicide, dicambe," vol. 95, 1995, p. 441, Abstract.
Weeks et al., "Characterization of a bacterial system capable of degrading dicambe and evluation of its potential in the development of herbicide-tolerant crops," J. Cell. Biochem., Supp. No. 18, part !, 1994, p. 91, Abstract.
95th ASM General Meeting, Session 177: Subsurface Microbiology and Transport Phenomena, Wednesday, 8:30am, 1995.
Batie; Chapter 18; Phthalate Dioxygenase Reductase and Related Flavin-Iron-Sulfur containing Electron Transferases, Chemical and Biochemistry of Flavoenzymes, vol. III, pp. 543-556, 1992.
Behrens; Genetic Engineering of Tobacco and Tomato Plants for Resistance to the Herbicide, Dicamba, 2003, Masters thesis, 185 pages.
Bernhardt; Chemical and Spectral Properties of Putidamonooxin, the Iron-Containing and Acid-Labile-Sulfur-Containing Monooxygenase of a 4-Methoxybenzoate O-Demethylase from *Pseudomonas putida*, 1978, Eur. I Biochem. 92, 209-223.
Bernhardt; A 4-Methoxybenzoate O-Demethylase from *Pseudomonas putida*. Eur. J. Biochem. 57, 241-256 (1975).
Bernhardt; Purification of a 4-Methoxybenzoate O-Demethylase from *Pseudomonas putida*, Hoppe-Seyler's Z. Physiol.Chem. 1971 Bd. 352, 1091-1099.
Biochemistry, Second Edition, Voet and Voet eds., John Wiley & Sons, Inc., New York, New York, 1995, pp. 125-130.
Brunel; Cloning and Sequencing of Pseudomonas Genes Encoding Vanillate Demethylase, Journal of Bacteriology, Oct. 1988, vol. 170, No. 1 0, p. 4924-4930.
Butler et al., Advances in Microbial Physiology, vol. 38, pp. 47-84, 1997.
Chrastil; The Role of Plasmids in the Degradation of the Herbicide, Dicamba, by *Pseudomonas maltophilia*, strain DI-6, Honors thesis, 2000, 52 pages.
Comai; Chloroplast Transport of a Ribulose Bisphosphate Carboxylase Small Subunit-5-enolpyruvyl 3-Phosphashikimate Synthase Chimeric Protein Requires Part of the Mature Small Subunit in addition to the Transit Peptide, 1988, The Journal of Biological Chemistry, vol. 263, No. 29, pp. 15104-14109.
Cork; Bioremediation of the Dicamba Variety of Chlorinated Aromatic Pesticides and Herbicides. Institute of Gas Technology, 1992. Gas, Oil, and Environmental Biotechnology V, pp. 427-442.
Cork; Microbial Transformations of Herbicides and Pesticides, Advances in Applied Microbiology, vol. 35, pp. 1-66, 1991.
Cork; Detection, Isolation, and Stability of Megaplasmid-Encoded Chloroaromic Herbicide-Degrading Genes within Pseudomonas Species, Advances in Applied Microbioligy, vol. 40, pp. 289-321, 1995.
Correll; Phthalate Dioxygenase Reductase: A Modular Structure for Electron Transfer from Pyridine Nucleotides to [2Fe-2S], Science, vol. 258. pp. 1604-1610, Dec. 4, 1992.
Craig; The Theoretical Possibility of Reverse Translation of Proteins into Genes, J. Theor. Biol. (1981) 88, 757-760.
Della-Cioppa; Translocation of the precursor of 5-enolpyruvylshikimate- 3-phosphate synthase into chloroplasts of higher plants in vitro, 1986, Proc. Natl. Acad. Sci. USA, vol. 83, pp. 6873-6877.
Fogarty; Bacterial Degradation of the Herbicide 3,6-Dichloro-2-Methoxybenzoic Acid (DICAMBA), 1991, Masters thesis, 122 pages.
Harayama et al. "Functional and Evolutionary Relationships Among Diverse Oxygenases", Annu. Rev. Microbiol. 1992, 46:565-601.
Gasser,' Genetically Engineering Plants for Crop Improvement, 1989, Science, vol. 244, p. 1293-1299.
Gibson, et al., "Aromatic hydrocarbon dioxygenases in environmental biotechnology", 2000, Current Opinion in Biotechnology, 11:236-243.
Gibson,' Toluene Dioxygenaase: A Multicomponent Enzyme System From *Pseudomonas putrida*, Oxygenases and Oxygen, 1982, Metabolism, pp. 51-62.
Horsch; A Simple and General Method for Transferring Genes into Plants. Science, vol. 227, No. 4691. pp. 1229-1231. Mar. 8, 1995.
Jiang et al. 1996, Journal of Bacteriology, 178(11): 3133-3139.
Junker et al., J. Bacteriology, vol. 179, No. 3, 1997, pp. 919-927.
Krueger; Aerobic and Anaerobic Soil Metabolism of Dicamba, J. Agric. Food Chem. 1991, 39:995-999.
Kruger; Development of a Microbe for Degradation of Dicamba (3,6-Dichloro-2-Methoxybenzoic Acid) 1984 Masters thesis, 66 pages.
Krueger; Development of Microbes for Degradation of the Herbicide Dicamba (3,6-Dichloro-2-Methoxybenzoic Acid) 1989 Ph.D. thesis, approved, 181 pages.
Krueger; Use of Dicamba-Degrading Microorganisms to Protect Dicamba Susceptible Plant Species, 1991, J. Agric Food chem, vol. 39, No. 5, 999-1002.
Krueger; Specificity of a Flavobacterium in metabolism of substituted chlorobenzoates, Journal of Industrial Microbiology, 5 (1990) 147-152.
Mason; The Electron-Transport Proteins of Hydroxylating Bacterial Dioxygenases, Annu. Rev. Microbiol. 1992; 46:277-305.
Neidle et al., J. Bacteriology, vol. 173, No. 17, 1991, pp. 5385-5395.
Schreier; The use of nuclear-encoded sequences to direct the light-regulated synthesis and transport of a foreign protein into plant, 1985, EMBO J. vol. 4, No. pp. 25-32.
Shah; Engineering Herbicide Tolerance in Transgenic Plants. Science, vol. 23.pp. 478-480, Jul. 25, 1986.
Simisnszky et al., Plant Biology, vol. 96, pp. 1750-1755, Feb. 1999.
Small; Alkene Monooxygenase from Xanthobacter Strain Py2, 1997, The Journal of Biological Chemistry vol. 272 No. 40, pp. 24913-24920.
Smith; Breakdown of the Herbicide Dicamba and Its Degradation Product 3,6-Dichlorosalicylic Acid in Prairie Soils, J. Agr. Food Chem., vol. 22, No. 4 1974, pp. 601-605.
Smith; Transformation of Dicamba in Regina Heavy Clay, 1973, J. Agr. Food Chem vol. 21, No. 4, 708-710.
Subramanian; Engineering dicamba selectivity in crops: a search for appropriate degradative enzymes( s), 1997, Journal of Industrial Microbiology & Biotechnology, 19:344-349.
Subramanian; Purification and Properties of Ferredoxin TOL, 1985, The Journal of Biological Chemistry vol. 260 No. 4, pp. 2355-2363.
Subramanian; Purification and Properties of NADH- Ferredoxin Reductase, The Journal of Biological Chemistry, 1981, vol. 256 No. 6, pp. 2723-2730.
Subramanian; Toluene Dioxygenase: Purification of An Iron-Sulfur Protein by Affinity Chromatography, Biochemical and Biophysical Research Communications, vol. 91, No. 3 1979, pp. 1131-1139.

Taraban; Degradation of Dicamba by an Anaerobic Consortium Enriched from Wetland Soil, Applied and Environmental Microbiology, Jul. 1993, p. 2332-2334.
van der Geize et al., 2002 Molecular Microbiology, 45(4): 1007-1018.
Oxygenases abstracts (1362-1367) FASEB Journal, May 21-25, 1995.
Weeks; Microbial Degradation of Dicamba: Potential Source of Genes for Development of Dicamba—Tolerant Crops., From the Fourth International Congress of Plant Molecular Biology Jun. 19-24, 1994 Amsterdam, The Netherlands,1 page.
Weising; Foreign Genes in Plants: Transfer, Structure, Expression, and Applications. Annu. Rev. Genet, 1988 22:421-477.
Werwath, et al., Characterisation of Sphingomonas sp. strain RW5 capable of degrading DICAMBA, UIB-GBF-CSIC-TUB-Symposium, Biodegradation of organic pollutants, Mallorca, 1996, p. 167.
Yang; Analysis of Dicamba Degradation by *Pseudomonas maltophilia* Using High-Performance Capillary Electrophoresis. Analytical Biochemistry 219, 37-42 (1994).
Yoch; Bacterial Iron-Sulfur Proteins, Microbiological Reviews, Sep. 1979, p. 384-421.
Supplementary European Search Report from Application No. EP 98915256.6 Mailed on Jul. 6, 2004.
International Preliminary Examination Report for PCT App No. PCT/US02/06310, Mailed Aug. 4, 2004.
International Search Report for PCT App No. PCT/US02/06310, Mailed Dec. 4, 2002.
Written Opinion for PCT App No. PCT/US02/06310, Mailed Mar. 17, 2004.
Duggleby "Identification of an acetolactate synthase small subunit gene in two eukaryotes", Gene 190(1997), pp. 245-249.
Fraley et al. "Expression of bacterial genes in plant cells", PNAS, vol. 80, pp. 4803-4807, Aug. 1993.
Yang et al., "Metabolism of Dicamba by *Pseudomonas maltophilla*, strain DI-6", Q-132, FASEB Journal, May 21-25, 1995, p. 422.
Behrens, M.R. et al.: "Dicamba resistance: Enlarging and preserving biotechnology-based weed management strategies", Science, vol. 316, No. 5828, pp. 1185-1188, May 25, 2007.
Complaint Demand for Jury Trial in US District Court District of Nebraska Case No. 4:04-cv-03356-RGK-DLP, filed Nov. 17, 2004, pp. 1-10.
Answer, Defenses and Counterclaims of BASF Corporation in US District Court District of Nebraska Case No. 4:04-cv-03356-RGK-DLP, filed Apr. 6, 2005, pp. 1-12.
Plaintiff'S Reply to Counterclaims in US District Court District of Nebraska Case No. 4:04-cv-03356-RGK-DLP, filed Apr. 25, 2005, pp. 1-7.
Defendant BASF Corporation's Memorandum in Support of Motion to Compel Plaintiff's Production of Documents and Information, to Extend Discovery Deadlines, and for Sanctions in US District Court District of Nebraska Case No. 4:04-cv-03356-RGK-DLP, filed Nov. 16, 2005, pp. 1-18.
Exhibit D of Affidavit of Charanjit Brahma in Support of BASF Corporation's Motion to Compel Plaintiff's Production of Documents and Information, to Extend Discovery Deadlines, and for Sanctions in US District Court District of Nebraska Case No. 4:04-cv-03356-RGK-DLP, filed Nov. 16, 2005, pp. 1-3.
Exhibit G of Affidavit of Charanjit Brahma in Support of BASF Corporation's Motion to Compel Plaintiff's Production of Documents and Information, to Extend Discovery Deadlines, and for Sanctions in US District Court District of Nebraska Case No. 4:04-cv-03356-RGK-DLP, filed Nov. 16, 2005, pp. 1-3.
Plaintiff's Brief in Opposition to Defendant's Motion to Compel and for Sanctions in US District Court District of Nebraska Case No. 4:04-cv-03356-RGK-DLP, filed Dec. 16, 2005, pp. 1-27.
Exhibit 1 of Index of Evidence in US District Court District of Nebraska Case No. 4:04-cv03356-RGK-DLP, filed Dec. 16, 2005.
Exhibit 4 of Index in US District Court District of Nebraska Case No. 4:04-cv-03356-RGK-DLP, filed Dec. 16, 2005.
Reply Brief in Support of Defendant BASF Corporation's Motion to Compel Plaintiff's Production of Documents and Information, to Extend Discovery Deadlines, and for Sanctions in US District Court District of Nebraska Case No. 4:04-cv03356-RGK-DLP, filed Dec. 23, 2005, pp. 1-17.
Exhibit P of Reply Brief in Support of Defendant BASF Corporation's Motion to Compel Plaintiff's Production of Documents and Information, to Extend Discovery Deadlines, and for Sanctions in US District Court District of Nebraska Case No. 4:04-cv-03356-RGK-DLP, filed Dec. 23, 2005, pp. 1-17.
Complaint in Intervention in US District Court District of Nebraska Case No. 4:04-cv-03356-RGK-DLP, filed Jan. 25, 2006, pp. 1-6.
Memorandum and Order in US District Court District of Nebraska Case No. 4:04-cv-03356-RGK-DLP, filed Sep. 6, 2006, pp. 1-9.
Draft Report of Planning Conference in US District Court District of Nebraska Case No. 4:04-cv-03356-RGK-DLP, filed Oct. 23, 2006, pp. 1-40.
Second Amended Complaint in Intervention in US District Court District of Nebraska Case No. 4:04-cv-03356-RGK-DLP, filed Dec. 1, 2006, pp. 1-11.
First Amended Answer in Intervention of Syngenta Crop Protection, Inc. to Monsanto Company's Amended Complaint in Intervention; and First Amended Counterclaim in US District Court District of Nebraska Case No. 4:04-cv-03356-RGK-DLP, filed Dec. 1, 2006, pp. 1-17.
Amended Complaint in US District Court District of Nebraska Case No. 4:04-cv-03356-RGK-DLP, filed Dec. 1, 2006, pp. 1-6.
Amended Answer and Defenses of BASF Corporation to Complaint of Plaintiff Board of Regents of the University of Nebraska and BASF Corporation'S Counterclaims and Cross-Claims in US District Court District of Nebraska Case No. 4:04-cv-03356-RGK-DLP, filed Dec. 1, 2006, pp. 1-19.
Reply of Intervening Plaintiff Monsanto Company to Amended Counterclaims of Defendant BASF Corporation in US District Court District of Nebraska Case No. 4:04-cv-03356-RGK-DLP, filed Dec. 18, 2006, pp. 1-9.
Plaintiff Board of Regents of the University of Nebraska's Reply to Counterclaims of BASF Corporation in US District Court District of Nebraska Case No. 4:04-cv-03356-RGK-DLP, filed Dec. 18, 2006, pp. 1-11.
Amended Complaint in US District Court District of Nebraska Case No. 4:04-cv-03356-RGK-DLP, filed Jan. 18, 2007, pp. 1-6.
Second Amended Complaint in Intervention in US District Court District of Nebraska Case No. 4:04-cv-03356-RGK-DLP, filed Jan. 18, 2007, pp. 1-11.
Exhibit A of Amended Complaint in US District Court District of Nebraska Case No. 4:04-cv-03356-RGK-DLP, filed Jan. 18, 2007, pp. 1-6.
Answer in Intervention of Syngenta Crop Protection, Inc. to Monsanto Company's Second Amended Complaint in Intervention; and Fist Amended Counterclaim and Crossclaim in US District Court District of Nebraska Case No. 4:04-cv-03356-RGK-DLP, filed Jan. 29, 2007, pp. 1-18.
Answer, Defenses, Counterclaims and Crossclaims of BASF Corporation to Amended Complaint of Plaintiff Board of Regents of the University of Nebraska in US District Court District of Nebraska Case No. 4:04-cv-03356-RGK-DLP, filed Jan. 29, 2007, pp. 1-22.
Amended Answer, Defenses and Counterclaims of BASF Corporation to Second Amended Complaint in Intervention of Monsanto Company in US District Court District of Nebraska Case No. 4:04-cv-03356-RGK-DLP, filed Jan. 29, 2007, pp. 1-22.
Reply of Intervening Plaintiff Monsanto Company to First Amended Counterclaim of Intervening Defendant Syngenta Crop Protection Inc. in US District Court District of Nebraska Case No. 4:04-cv-03356-RGK-DLP, filed Feb. 14, 2007, pp. 1-9.
Reply of Intervening Plaintiff Monsanto Company to Amended Counterclaims of Defendant BASF Corporation in US District Court District of Nebraska Case No. 4:04-cv-03356-RGK-DLP, filed Feb. 14, 2007, pp. 1-7.
Plaintiff Board of Regents of the University of Nebraska's Reply to Amended Counterclaim of BASF Corporation in US District Court District of Nebraska Case No. 4:04-cv-03356-RGK-DLP, filed Feb. 15, 2007, pp. 1-12.
Plaintiff Board of Regents of the University of Nebraska's Reply to Amended Counterclaim and Answer to Amended Crossclaim of Syngenta Crop Protection, Inc. In US District Court District of Nebraska Case No. 4:04-cv-03356-RGK-DLP, filed Feb. 15, 2007, pp. 1-10.

Syngenta Crop Protection, Inc.'s Reply to BASF Corporation's Cross-Claims in US District Court District of Nebraska Case No. 4:04-cv-03356-RGK-DLP, filed Feb. 22, 2007, pp. 1-13.

Exhibit A of Index of Evidence in Support of Intervening Plaintiff's Motion for Protective Order in US District Court District of Nebraska Case No. 4:04-cv-03356-RGK-DLP, filed Mar. 6, 2007, pp. 1-11.

Exhibit F of Defendant BASF Corporation's Memorandum in Opposition to Intervening Plaintiff's Motion for Protective Order in US District Court District of Nebraska Case No. 4:04-cv-03356-RGK-DLP, filed Mar. 23, 2007, pp. 1-24.

Exhibit A of Defendant BASF Corporation's Memorandum in Opposition to Intervening Plaintiff's Motion for Protective Order in US District Court District of Nebraska Case No. 4:04-cv-03356-RGK-DLP, filed Mar. 23, 2007, pp. 1-25.

Exhibit B of Defendant BASF Corporation's Memorandum in Opposition to Intervening Plaintiff's Motion for Protective Order in US District Court District of Nebraska Case No. 4:04-cv-03356-RGK-DLP, filed Mar. 23, 2007, pp. 1-26.

Exhibit D of Defendant BASF Corporation's Memorandum in Opposition to Intervening Plaintiff's Motion for Protective Order in US District Court District of Nebraska Case No. 4:04-cv-03356-RGK-DLP, filed Mar. 23, 2007, pp. 1-27.

Exhibit E of Defendant BASF Corporation's Memorandum in Opposition to Intervening Plaintiff's Motion for Protective Order in US District Court District of Nebraska Case No. 4:04-cv-03356-RGK-DLP, filed Mar. 23, 2007, pp. 1-28.

Brief in Support of Plaintiff's Motion for Partial Summary Judgement, in US District Court District of Nebraska Case No. 4:04-cv-03356-RGK-DLP, filed May 25, 2007, pp. 1-28.

Stipulation of Agreed Claim Constructions of the Board of Regents of the University of Nebraska, BASF Corporation, and Monsanto Company in US District Court District of Nebraska Case No. 4:04-cv-03356-RGK-DLP, filed May 25, 2007, pp. 1-7.

Exhibit 1 of Plaintiff University's Index of Evidence in Opposition to BASF's Motion for Summary Judgement (No. 1) and Syngenta's Motion for Partial Summary Judgement in in US District Court District of Nebraska Case No. 4:04-cv-03356- RGK-DLP, filed Jun. 18, 2007, pp. 1-13.

Defendant BASF Corporations Responses to Intervening Plaintiff Monsanto Company's First Set of Requests for Admission (Nos. 1-150) in US District Court District of Nebraska Case No. 4:04-cv-03356-RGK-DLP, dated Oct. 12, 2007, pp. 1-51.

Defendant BASF Corporations Second Amended Responses to Intervening Plaintiff Monsantos Company's First Set of Interrogatories (Nos. 1 and 2) in US District Court District of Nebraska Case No. 4:04-cv-03356-RGK-DLP, dated Oct. 12, 2007, pp. 1-.

Memorandum and Order in US District Court District of Nebraska Case No. 4:04-cv-03356-RGK-DLP, filed Nov. 5, 2007, pp. 1-14.

Memorandum and Order in US District Court District of Nebraska Case No. 4:04-cv-03356-RGK-DLP, filed Nov. 6, 2007, pp. 1-35.

Memorandum and Order in US District Court District of Nebraska Case No. 4:04-cv-03356-RGK-DLP, filed Dec. 12, 2007, pp. 1-6.

Memorandum and Order in US District Court District of Nebraska Case No. 4:04-cv-03356-RGK-DLP, filed Apr. 29, 2008, pp. 1-5.

Memorandum and Order in US District Court District of Nebraska Case No. 4:04-cv-03356-RGK-DLP, filed Oct. 14, 2008, pp. 1-4.

Memorandum and Order in US District Court District of Nebraska Case No. 4:04-cv-03356-RGK-DLP, filed Oct. 21, 2008, pp. 1-3.

Order on Final Pretrial Conference in US District Court District of Nebraska Case No. 4:04-cv-03356-RGK-DLP, filed Oct. 30, 2008, pp. 1-16.

Exhibit 2 of Order on Final Pretrial Conference in US District Court District of Nebraska Case No. 4:04-cv-03356-RGK-DLP, filed Oct. 30, 2008, pp. 1-17.

Joint Motion and Stipulation of Dismissal in US District Court District of Nebraska Case No. 4:04-cv-03356-RGK-DLP, filed Nov. 7, 2008, pp. 1-4.

Order in US District Court District of Nebraska Case No. 4:04-cv-03356-RGK-DLP, filed Nov. 7, 2008, pp. 1-2.

Intervening Defendant Syngenta Crop Protection Inc.'s Trial Brief in US District Court District of Nebraska Case No. 4:04-cv-03356-RGK-DLP, filed Nov. 10, 2008, pp. 1-36.

Joint Motion and Stipulation of Dismissal in US District Court District of Nebraska Case No. 4:04-cv-03356-RGK-DLP, filed Nov. 16, 2008, pp. 1-4.

Memorandum and Order in US District Court District of Nebraska Case No. 4:04-cv-03356-RGK-DLP, filed Nov. 17, 2008, pp. 1-2.

Judgement in US District Court District of Nebraska Case No. 4:04-cv-03356-RGK-DLP, filed Nov. 17, 2008, 1 page.

* cited by examiner

FIG. 2

```
fer6_rhoca   - A K I I F I E H N   G T R H E V E A K P   G L T V M E A A R D   N G V P G I   35
 fer_caucr   M A K I T Y I Q H D   G A E Q V I D V K P   G L T V M E G A V K   N N V P G I   36
 thcc_rhoer  - P T V T Y V H P D   G T K H E V E V P T   G K R V M Q A A I G   A G I D G I   35
 putx_psepu  - S K V V Y V S H D   G T R R E L D V A D   G V S L M Q A A V S   N G I Y D I   35
 terp_psesp  - P R V V F I D E Q   S G E Y A V D A Q D   G Q S L M E V A T Q   N G V P G I   35
   ferr_di6  M P Q I T V V N Q S   G E E S S V E A S E   G R T L M E V I R D   S G F D E L   36
                                          ─────1─────                              ─────2───── fer6_rhoca   D A D C G G A C A C   S T C H A Y V D P A   W V D K L P K A L P   T E T D M L   71
 fer_caucr   D A D C G G A C A C   A T C H V Y V D E A   W L D K T G D K S A   M E E S M L   72
 thcc_rhoer  V A E C G G Q A M C   A T C H V Y V E S P   W A D K F P S I S E   E E D E M L   71
 putx_psepu  V G D C G G S A S C   A T C H V Y V N E A   F T D K V P A A N E   R E I G M L   71
 terp_psesp  V A E C G G S C V C   A T C R I E L E D A   W V E I V G E A N P   D E N D L L   71
   ferr_di6  L A L C G G C C S C   A T C H V H I D P A   F M D K L P E M S E   D E N D L L   72
                                          ─────3───── fer6_rhoca   D F A Y E P N P A T   S R L T C Q I K V T   S L L D G L V V H L   P E K Q I 106
 fer_caucr   D F A E N V E P . N   S R L S C Q I K V S   D A L D G L V V R L   P E S Q H 106
 thcc_rhoer  D D T V S P R T E A   S R L S C Q L V V S   D D V D G L I V R L   P E E Q V 106
 putx_psepu  E C V T A E L K P N   S R L C C Q I I M T   P E L D G I V V D V   P D R Q W 106
 terp_psesp  Q S T G E P M T A G   T R L S C Q V F T D   P S M D G L I V R V   P L P A - 105
   ferr_di6  D S S . D H R N E Y   S R L S C Q I P V T   G A L E G I K V T I   A Q E D - 105
```

```
              1
red1_di6  --MSKADVVI VGAGHQGAQC AIALRQNGFE GTITVIGREP EYPYERPPLS KEYFA  53
red2_di6  --MQRADVVI VGAGHQGAQC AIALRQNGFE GTITVIGREP EYPYERPPLS KEYFA  53
aj002606  --MRSADVVI VGAGHAGAQC AIALRQAGFE GSIALVGREN EVPYERPPLS KEYFS  53
thcd_rhoer -----SKVI TGSGQAGFKA AVSLRSHGFS GTITLVGDEP GVPYQRPPLS KAYLH   49
cama_psepu -MNANDNVVI VGTGLAGVKV AFGLRASGVE GNIRLVGDAT VIPHHLPPLS KAYLA   54
tera_psesp MGERRDTTVI VGAGHAGTAA AFFLREFGKH GRVLLCSAET QHPYQRPPLS KEYLL   55

2
red1_di6  REKTFDRLYI RPPTFWAEKN IEFKLGTEVT KVDPKAHELT LSNGESYGYQ KLVWA 108
red2_di6  REKTFDRLYI RPPTFWAEKN IEFKLGTEVT KVDPKAHELT LSNGESYGYQ KLVWA 108
aj002606  REKSFERLYI RPPEFWREKD IHLTLGIEVS AVDPGSKVLT LSDGSAWAYQ QLVWA 108
thcd_rhoer SDPDRESLAL RPAQYFDDHR TTLTCGKPVV RIDRDAQRVE LIDATAIEYD HLTLA 104
cama_psepu GKATAESLYL RTPDAYAAQN IQLLGGTQVT AINRDRQQVI LSDGRALDYD RLVLA 109
tera_psesp AQHSTPSI.L KGKDSYARAD IELCLQDDVL SITPASRQVK SSQG.SYTYD HLVLA 108

2                                           3
red1_di6  TGGDPRRLSC .QGA...DLTG IHAVRTREDC DTLMAEVDAG TKNIVVIGGG YIGLE 160
red2_di6  TGGDPRRLSC .QGA...DLTG IHAVRTREDC DTLMAEVDAG TKNIVVIGGG YIGLE 160
aj002606  TGGDPRKLAC .PGA...SLSG VHATRTRADC DRLMAEIDRG LTQVVVVGGG YIGLE 160
thcd_rhoer TGARNRLLPV .PGA...NLPG VHYLRTAGEA ESLTSSM.AS CSSLVVIGAG IGLE  155
cama_psepu TGGRPRPLPV ASGAVGKANN FRYLRTLEDA ACIRRQLIAD .NRLVVIGGG YIGLE 163
tera_psesp TGSHPRFMA. ...TLGQADN LCYLSDWDDA GRKRQQL.GE ASRIVVVGGG IGLE  158

3
red1_di6  AAAVLSKMGL KVTLLEALPR VLARVAGEDL STFYQKEHVD HGVDLRTEVM VD..S 213
red2_di6  AAAVLSKMGL KVTLLEALPR VLARVAGEDL STFYQKEHVD HGVDLRTEVM VD..S 213
aj002606  AAAVLTKINC HVTLLEAMPR VLARVAGTEL STFYENEHRG HGVDLRTGIT VA...A 213
thcd_rhoer VAAAARKKGL DVTVVEAMDR PMARALSSVM SGYFSTAHTE HGVHMRLSTQ VK...T 208
cama_psepu VAATAIKANM HVTLLDTAAR VLERVTAPPV SAFYEHLHRE AGVDIRTGTQ VCGFE 218
tera_psesp IASSACKMGK HVTVKERAPR LLSRVVSEAF ATFIGDIHLG NGIKELRLGEE VREVR 213

4
red1_di6  LVGENGKVTG VQLAGGEVIP ASGVIVGIGI VPAVGPLIAA GAAGANGVDV DEYCR 268
red2_di6  LVGENGKVTG VQLAGGEVIP ASGVIVGIGI VPAIGPLIAA GAAGANGVDV DEYCR 268
aj002606  LEGQE.SVTG VRLGDGSVLP AQAVIVGIGI VPAVAPLIEA GAAGDGVTV  DEYCR 267
thcd_rhoer INAADGRAAG VTTNSGDVIH ADAVVVGIGV VPNIELAALT GLPVDNGIVV DEYLR 263
cama_psepu MSTDQQKVTA VLCEDGTRLP ADLVIAGIGI IPNCELASAA GLQVDNGIVI NEHMQ 273
tera_psesp RCTSGVRVDA VFLSDGQLLE CDMLVIGVGS EPRMELATAA GLACASGVLV DERCH 268

5
red1_di6  TSLPDIYAIG DCAAFACDYA GGNVMRVESV QNANDMGTCV AKAICGDEKP YKAFP 323
red2_di6  TSLPDIYAIG DCAAFACDYA GGNVMRVESV QNANDMGTCV AKAICGDEKP YKAFP 323
aj002606  TSLPDVFAIG DCABFSCSFA DGRVLVRVESV QNANDQABCV AKTICGDPQP YRAFP 322
thcd_rhoer TPDENISAIG DCAAYPIPGK AG.LVRLESV QNAVDQARCL AAQLTGTSTH YRSVP 317
cama_psepu TSDPLIMAVG DCAREHSQLY D.RWVRLESV PNALDQARKL AAILCGKVPR DEAAP 327
tera_psesp TSDPFISAIG DCVAV.CPSP GHQLPRRESV QNATKQARLV AARLSGRPVE PVQTP 322 red1_di6  WFWSNQYDLK LQTAGINLGF DKTVIRGNPE ERSFSVVYLK DGRVVALDCV NMVKD 378
red2_di6  WFWSNQYDLK LQTAGINLGF DKTVIRGNPE ERSFSVVYLK DGRVVALDCV NMVKD 378
aj002606  WFWSNQYDLK LQTAGLSLGY DQTVVRGDPA VRSFSVLYLK QGRVVALDCV NMVKD 377
thcd_rhoer WFWSEQYESK LQMAGLTAGA DTHVVRGSVD SGVFSIFCFL GTRLLGVESV NKPKD 372
cama_psepu WFWSDQYEIG LKMVGLSEGY DRIKVRGSLA QPDFSVFYLQ GDRVLAVDTV NRPVE 382
tera_psesp WFWSDQLQAM INLAGERPAQ GQVIVRRYGG DK.VSMLYLQ DQQLVAKKAC NMPGD 376 red1_di6  YVQGRKLVEA GATPDLEALA DAGKPLKELI *--------- ---------- ----408
red2_di6  YVQGRKLVEA GATPDLEALA DAGKPLKELQ Y*-------- ---------- ----409
aj002606  YVQGRKLVEA NVCVSPEQLV DTGLALKDLI PV-------- ---------- ----409
thcd_rhoer HMAARKILAT EMPLTPEQAA DTDFDLKLAI ARHKDTHKDE VASADIGERQ VVAS426
cama_psepu PNQSKQTKTD RLPVEPNLLG DESVPLKETI AAAKAELSSA ---------- ----422
tera_psesp CLLARRALGQ NHSLDLARLV DADVPLKDAI HFA------- ---------- ----409
```

METHODS AND MATERIALS FOR MAKING AND USING TRANSGENIC DICAMBA-DEGRADING ORGANISMS

This application is a divisional of U.S. application Ser. No. 09/797,238, filed Feb. 28, 2001 now U.S. Pat. No. 7,105,724, which is a continuation-in-part of U.S. application Ser. No. 09/055,145, filed Apr. 3, 1998 now U.S. Pat. No. 7,022,896, which claims benefit of priority under 35 U.S.C. §119(e) to U.S. Provisional Application Ser. Nos. 60/042,666 and 60/042,941, both filed Apr. 4, 1997. The complete disclosures of all of the above-identified applications are incorporated herein by reference.

GOVERNMENT SUPPORT

This invention was made in part with government support under Grant No. OR22072-86, awarded by the Consortium of Plant Biotechnology Research. The government has certain rights in the invention.

FIELD OF THE INVENTION

The present invention relates to transgenic organisms that are able to degrade the herbicide dicamba, including transgenic plants that have been made tolerant to dicamba. The invention also relates to dicamba-degrading enzymes and to DNA molecules and DNA constructs coding for dicamba-degrading enzymes. The invention further relates to a method of controlling weeds in fields of dicamba-tolerant transgenic plants and to a method of removing dicamba from materials contaminated with it (bioremediation). Finally, the invention relates to methods of selecting transformants based on dicamba tolerance or on detecting the fluorescence of 3,6-dichlorosalicylic acid which is generated as a result of dicamba degradation.

BACKGROUND

Herbicides are used routinely in agricultural production. Their effectiveness is often determined by their ability to kill weed growth in crop fields and the tolerance of the cash crop to the herbicide. If the cash crop is not tolerant to the herbicide, the herbicide will either diminish the productivity of the cash crop or kill it altogether. Conversely, if the herbicide is not strong enough, it may allow too much weed growth in the crop field which will, in turn, lessen the productivity of the cash crop. Therefore, it is desirable to produce economically important plants which are tolerant to herbicides. To protect the water and environmental quality of agricultural lands, it is also desirable to develop technologies to degrade herbicides in cases of accidental spills of the herbicide or in cases of unacceptably high levels of soil or water contamination.

Genes encoding enzymes which inactivate herbicides and other xenophobic compounds have previously been isolated from a variety of procaryotic and eucaryotic organisms. In some cases, these genes have been genetically engineered for successful expression in plants. Through this approach, plants have been developed which are tolerant to the herbicides 2,4-dichlorophenoxyacetic acid (Streber and Willmitzer (1989) *Bio/Technology* 7:811-816; 2,4-D), bromoxynil (Stalker et al. (1988) *Science* 242:419-423; tradename Buctril), glyphosate (Comai et al. (1985) *Nature* 317:741-744; tradename Round-Up) and phosphinothricin (De Block et al. (1987) *EMBO J.* 6:2513-2518; tradename Basta).

Dicamba (tradename Banvel) is used as a pre-emergent and post-emergent herbicide for the control of annual and perennial broadleaf weeds and several grassy weeds in corn, sorghum, small grains, pasture, hay, rangeland, sugarcane, asparagus, turf and grass seed crops. See *Crop Protection Reference*, pages 1803-1821 (Chemical & Pharmaceutical Press, Inc., New York, NY, 11th ed., 1995). Unfortunately, dicamba can injure many commercial crops (including beans, soybeans, cotton, peas, potatoes, sunflowers, tomatoes, tobacco, and fruit trees), ornamental plants and trees, and other broadleaf plants when it comes into contact with them. Id. Dicamba is chemically stable and can sometimes be persistent in the environment.

Dicamba is in the class of benzoic acid herbicides. It has been suggested that plants tolerant to benzoic acid herbicides, including dicamba, can be produced by incorporating a 1-aminocyclopropane-1-carboxylic acid (ACC) synthase antisense gene, an ACC oxidase antisense gene, an ACC deaminase gene, or combinations thereof, into the plants. See Canadian Patent Application 2,165,036 (published Jun. 16, 1996). However, no experimental data are presented in this application which demonstrate such tolerance.

Bacteria that metabolize dicamba are known. See U.S. Pat. No. 5,445,962; Krueger et al., *J. Agric. Food Chem.*, 37, 534-538 (1989); Cork and Krueger, *Adv. Appl. Microbiol.*, 38, 1-66 (1991); Cork and Khalil, *Adv. Appl. Microbiol.*, 40, 289-320 (1995). It has been suggested that the specific genes responsible for dicamba metabolism by these bacteria could be isolated and used to produce dicamba-resistant plants and other organisms. See id and Yang et al., *Anal. Biochem.*, 219:37-42 (1994). However, prior to the present invention, no such genes had been identified or isolated.

SUMMARY OF THE INVENTION

The invention provides an isolated and at least partially purified dicamba-degrading O-demethylase, an isolated and at least partially purified dicamba-degrading oxygenase, an isolated and at least partially purified dicamba-degrading ferredoxin, and an isolated and at least partially purified dicamba-degrading reductase, all as defined and described below.

The invention also provides an isolated DNA molecule comprising a DNA sequence coding for a dicamba-degrading oxygenase, an isolated DNA molecule comprising a DNA sequence coding for a dicamba-degrading ferredoxin, and an isolated DNA molecule comprising a DNA sequence coding for a dicamba-degrading reductase. The invention further provides a DNA construct comprising a DNA sequence coding for a dicamba-degrading oxygenase, a DNA sequence coding for a dicamba-degrading ferredoxin, or a DNA sequence coding for a dicamba-degrading reductase, each DNA coding sequence being operatively linked to expression control sequences. In addition, the invention provides a DNA construct comprising a DNA sequence coding for a dicamba-degrading oxygenase, a DNA sequence coding for a dicamba-degrading ferredoxin, and a DNA sequence coding for a dicamba-degrading reductase, each DNA coding sequence being operatively linked to expression control sequences.

The invention further provides a transgenic host cell comprising DNA coding for a dicamba-degrading oxygenase, DNA coding for a dicamba-degrading ferredoxin, or DNA coding for a dicamba-degrading reductase, each DNA being operatively linked to expression control sequences. In addition, the invention provides a transgenic host cell comprising DNA coding for a dicamba-degrading oxygenase and DNA coding for a dicamba-degrading ferredoxin, DNA coding for a dicamba-degrading reductase, or DNA coding for a dicamba-degrading ferredoxin and DNA coding for a dicamba-degrading reductase, each DNA being operatively linked to expression control sequences. The transgenic host cell may be a plant cell or a prokaryotic or eukaryotic microorganism.

The invention also provides a transgenic plant or plant part comprising one or more cells comprising DNA coding for a dicamba-degrading oxygenase, DNA coding for a dicamba-degrading ferredoxin, or DNA coding for a dicamba-degrading reductase, each DNA being operatively linked to expression control sequences. The invention further provides a transgenic plant or plant part comprising one or more cells comprising DNA coding for a dicamba-degrading oxygenase and DNA coding for a dicamba-degrading ferredoxin, DNA coding for a dicamba-degrading reductase, or DNA coding for a dicamba-degrading ferredoxin and DNA coding for a dicamba-degrading reductase, each DNA being operatively linked to expression control sequences. The transgenic plant or plant part is preferably tolerant to dicamba or has had its tolerance to dicamba increased as a result of the expression of the dicamba-degrading enzyme(s).

The invention also provides a method of controlling weeds in a field containing transgenic dicamba-tolerant plants. The method comprises applying an amount of dicamba to the field which is effective to control the weeds.

The invention further provides methods of decontaminating a material containing dicamba. In one embodiment, the method comprises applying an effective amount of a transgenic dicamba-degrading microorganism to the material. In another embodiment, the method comprises applying an effective amount of a dicamba-degrading O-demethylase or of a combination of a dicamba-degrading oxygenase, a dicamba-degrading ferredoxin and a dicamba-degrading reductase to the material.

The invention also provides a method of selecting transformed plant cells and transformed plants using dicamba tolerance as the selection marker. In one embodiment, the method comprises transforming at least some of the plant cells in a population of plant cells so that they are tolerant to dicamba and growing the resulting population of plant cells in a culture medium containing dicamba at a concentration selected so that transformed plant cells will grow and untransformed plant cells will not grow. In another embodiment, the method comprising applying dicamba to a population of plants suspected of comprising plants that have been transformed so that they are tolerant to dicamba, the dicamba being applied in an amount selected so that transformed plants will grow, and the growth of untransformed plants will be inhibited.

Finally, the invention provides a method of selecting, or screening for, transformed host cells, intact organisms, and parts of organisms. The method comprises providing a population of host cells, intact organisms, or parts of organisms suspected of comprising host cells, intact organisms, or parts of organisms that have been transformed so that they are able to degrade dicamba, contacting the population of host cells, intact organisms, or parts of organisms with dicamba, and ascertaining the presence or level of fluorescence due to 3,6-dichlorosalicylic acid. The 3,6-dichlorosalicylic acid is generated in transformed host cells, intact organisms, or parts of organisms as a result of the degradation of dicamba, but will not be generated in untransformed host cells, intact organisms, or parts of organisms.

BRIEF DESCRIPTION OF THE DRAWINGS

FIG. 2. Comparison of the derived amino acid sequence of the ferredoxin component of dicamba 0-demethylase to the amino acid sequences of members of the adrenodoxin family of ferredoxins. In FIG. 2, ferr di6 =ferredoxin component of dicamba O-demethylase from *Pseudomonas maltophilia* DI-6 [SEQ ID NO:5]; fer6 rhoca =ferredoxin from *Rhodobacter capsulatus* [SEQ ID NO:10]; fer caucr =ferredoxin from *Caulobacter crescentus* [SEQ ID NO:11 ]; thcc rhocr =ferredoxin from *Rhodococcus erythropolis* [SEQ IDNO:12]; putx psepu =ferredoxin from *Pseudomonas putida* [SEQ ID NO:13]; terp psesp =ferredoxin from *Pseudomonas* sp.[SEQ ID NO:14]. Also in FIG. 2, the numbers 1-3 designate the three conserved motifs of the adrenodoxin family of bacterial ferredoxins.

FIG. 3. Comparison of the derived amino acid sequence of the two reductase components of dicamba O-demethylase to the amino acid sequences of members of the family of FAD-dependent pyridine nucleotide reductases. In FIG. 3, red1 di6 -reductase component of dicamba O-demethylase from *P. maltophilia* DI-6 [SEQ ID NO:7]; red2 di6 =reductase component of dicamba O-demethylase from *P. maltophilia* DI-6 [SEQ ID NO:9]; AJ002606 =reductase from *Sphingomonas* sp. [SEQ ID NO:15]; thcd rhoer =reductase from *R. erythropolis* [SEQ ID NO:16]; camapsepu=reductase from *P. putida* [SEQ ID NO:17]; tera pscsp =reductase from *Pseudomonas* sp. [SEQ ID NO:18]. Also in FIG. 3, the numbers 1-5 designate the five conserved motifs of FAD-dependent pyridine nucleotide reductases.

DETAILED DESCRIPTION OF THE PRESENTLY PREFERRED EMBODIMENTS OF THE INVENTION

Figure 1:
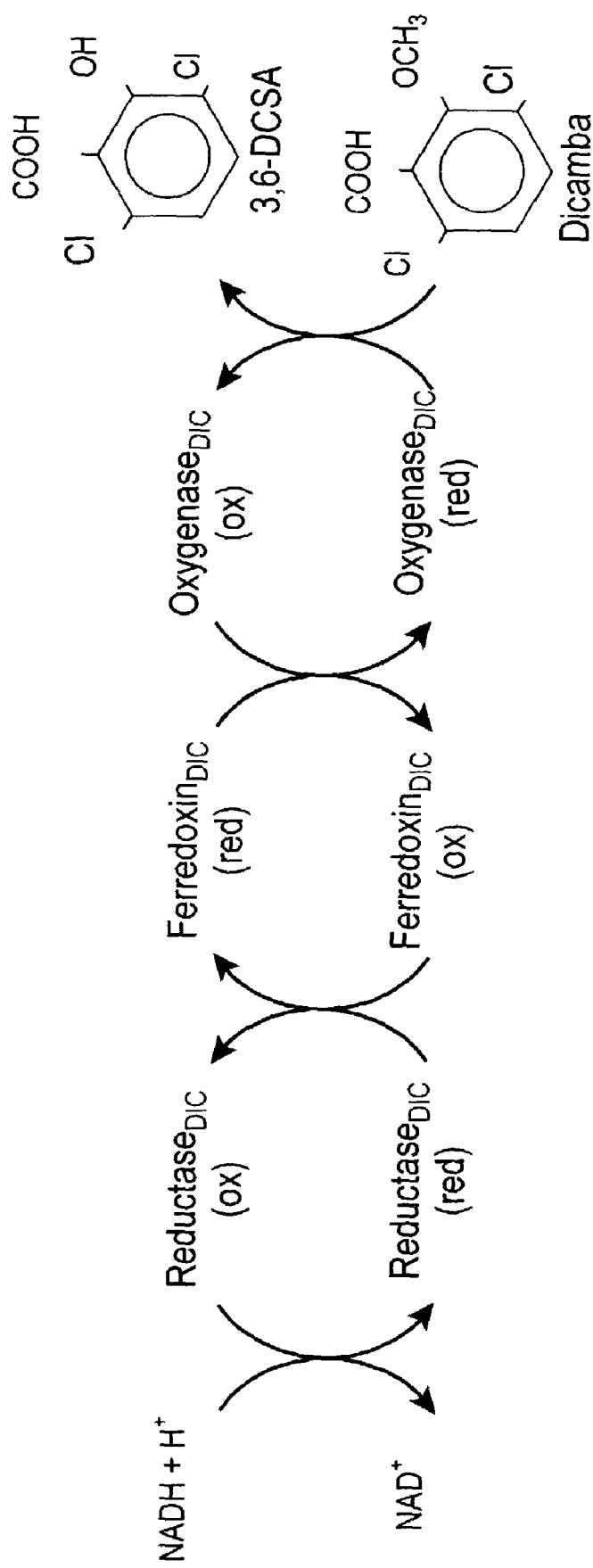
FIG. 1. A diagram of the proposed electron transport scheme for dicamba O-demethylase. Electrons from NADH are transferred sequentially from reductase$_{DIC}$ to ferredoxin$_{DIC}$ and then to oxygenase$_{DIC}$. The reaction of oxygen with the substrate dicamba to form 3,6-dichlorosalicylic acid is catalyzed by oxygenase$_{DIC}$. ox, oxidized; red, reduced.

Prior studies (Cork and Kreuger, *Advan. Appl. Microbiol.* 36:1-56 and Yang et al. (1994) *Anal. Biochem.* 219:37-42) have shown that the soil bacterium, *Pseudomonas maltophilia*, strain DI-6, is capable of destroying the herbicidal activity of dicamba through a single step reaction in which dicamba (3,6-dichloro-2-methoxybenzoic acid) is converted to 3,6-dichlorosalicylic acid (3,6-DCSA). 3,6-DCSA has no herbicidal activity and has not been shown to have any detrimental effects on plants. In addition, 3,6-DCSA is readily degraded by the normal bacterial flora present in soil.

The experiments described herein confirm the hypothesis of Yang et al. (see id.) that an O-demethylase is responsible for the conversion of dicamba to 3,6-DCSA by *P. maltophilia* strain DI-6 and establish that the O-demethylase is a three-component enzyme system consisting of a reductase, a ferredoxin, and an oxygenase. See Examples 1 and 3 which describe in detail the isolation, purification and characterization of the *P. maltophilia* O-demethylase and its three components. The reaction scheme for the reaction catalyzed by the three components of dicamba O-demethylase is presented in FIG. 1. As illustrated in FIG. 1, electrons from NADH are shuttled through a short electron chain consisting of the reductase and ferredoxin to the terminal oxygenase which catalyzes the oxidation of dicamba to produce 3,6-DCSA.

In a first embodiment, the invention provides isolated and at least partially purified dicamba-degrading enzymes. "Isolated" is used herein to mean that the enzymes have at least been removed from the cells in which they are produced (i.e., they are contained in a cell lysate). "At least partially purified"

is used herein to mean that they have been separated at least partially from the other components of the cell lysate. Preferably, the enzymes have been purified sufficiently so that the enzyme preparations are at least about 70% homogenous.

In particular, the invention provides an isolated and at least partially purified dicamba-degrading O-demethylase. "Dicamba-degrading O-demethylase" is defined herein to mean a combination of a dicamba-degrading oxygenase, a dicamba-degrading ferredoxin and a dicamba-degrading reductase, all as defined below.

The invention also provides an isolated and at least partially purified dicamba-degrading oxygenase. "Dicamba-degrading oxygenase" is defined herein to mean the oxygenase purified from *P. maltophilia* strain DI-6 and oxygenases which have an amino acid sequence which is at least about 65% homologous, preferably at least about 85% homologous, to that of the *P. maltophilia* oxygenase and which can participate in the degradation of dicamba. "Dicamba-degrading oxygenases" include mutant oxygenases having the amino acid sequence of the *P. maltophilia* oxygenase wherein one or more amino acids have been added to, deleted from, or substituted for, the amino acids of the *P. maltophilia* oxygenase sequence. Activity of dicamba-degrading oxygenases can be determined as described in Examples 1 and 3.

The invention further provides an isolated and at least partially purified dicamba-degrading ferredoxin. "Dicamba-degrading ferredoxin" is defined herein to mean the ferredoxin purified from *P. maltophilia* strain DI-6 and ferredoxins which have an amino acid sequence which is at least about 65% homologous, preferably at least about 85% homologous, to that of the *P. maltophilia* ferredoxin and which can participate in the degradation of dicamba. "Dicamba-degrading ferredoxins" include mutant ferredoxins having the amino acid sequence of the *P. maltophilia* ferredoxin wherein one or more amino acids have been added to, deleted from, or substituted for, the amino acids of the *P. maltophilia* ferredoxin sequence. Activity of dicamba-degrading ferredoxins can be determined as described in Examples 1 and 3.

Finally, the invention provides an isolated and at least partially purified dicamba-degrading reductase. "Dicamba-degrading reductase" is defined herein to mean the reductases purified from *P. maltophilia* strain DI-6 and reductases which have an amino acid sequence which is at least about 65% homologous, preferably at least about 85% homologous, to that of one of the *P. maltophilia* reductases and which can participate in the degradation of dicamba. "Dicamba-degrading reductases" include mutant reductases having the amino acid sequence of one of the *P. maltophilia* reductases wherein one or more amino acids have been added to, deleted from, or substituted for, the amino acids of the *P. maltophilia* reductase sequence. Activity of dicamba-degrading reductases can be determined as described in Examples 1 and 3.

Methods of determining the degree of homology of amino acid sequences are well known in the art. For instance, the FASTA program of the Genetics Computing Group (GCG) software package (University of Wisconsin, Madison, Wis.) can be used to compare sequences in various protein databases such as the Swiss Protein Database.

The dicamba-degrading enzymes of the invention can be isolated and purified as described in Examples 1 and 3 from *P. maltophilia* or other organisms. Suitable other organisms include bacteria other than *P. maltophilia* strain DI-6 that degrade dicamba. Several strains of such bacteria are known. See U.S. Pat. No. 5,445,962; Krueger et al., *J. Agric. Food Chem.*, 37, 534-538 (1989); Cork and Krueger, *Adv. Appl. Microbiol.*, 38, 1-66 (1991); Cork and Khalil, *Adv. Appl. Microbiol.*, 40, 289-320 (1995). Other dicamba-degrading bacterial strains can be isolated as were these strains by methods well known in the art.

Preferably, however, the dicamba-degrading enzymes of the invention are prepared using recombinant DNA techniques (see below). In particular, mutant enzymes having the amino acid sequence of the *P. maltophilia* enzyme wherein one or more amino acids have been added to, deleted from, or substituted for, the amino acids of the *P. maltophilia* sequence are prepared in this manner using, for example, oligonucleotide-directed mutagenesis, linker-scanning mutagenesis, mutagenesis using the polymerase chain reaction, and the like. See Ausubel et al. (eds.), *Current Protocols In Molecular Biology* (Wiley Interscience 1990) and McPherson (ed.), *Directed Mutagenesis: A Practical Approach* (IRL Press 1991).

In a second embodiment, the invention provides isolated DNA molecules coding for dicamba-degrading enzymes of the invention. "Isolated" is used herein to mean that the DNA molecule has been removed from its natural environment or is not a naturally-occurring DNA molecule. Methods of preparing these DNA molecules are well known in the art. See, e.g., Maniatis et al., *Molecular Cloning: A Laboratory Manual*, Cold Spring Harbor, NY (1982), Sambrook et al., *Molecular Cloning: A Laboratory Manual*, Cold Spring Harbor, NY (1989).

For instance, the DNA molecules of the invention may be isolated cDNA or genomic clones. The identification and isolation of clones coding for the dicamba-degrading enzymes of *P. maltophilia* strain DI-6 are described in Examples 2 and 4-5. Additional clones coding for dicamba-degrading enzymes can be obtained in a similar manner. The isolated clones, or portions of them, can be used as probes to identify and isolate additional clones from organisms other than the ones from which the clones were originally isolated. Suitable organisms include bacteria that degrade dicamba. As noted above, in addition to *P. maltophilia* strain DI-6, several strains of bacteria are known that degrade dicamba. See U.S. Pat. No. 5,445,962; Krueger et al., *J. Agric. Food Chem.*, 37, 534-538 (1989); Cork and Krueger, *Adv. Appl. Microbiol.*, 38, 1-66(1991); Cork and Khalil, *Adv. Appl. Microbiol.*, 40, 289-320 (1995).

The DNA molecules of the invention can also be chemically synthesized using the sequences of isolated clones. Such techniques are well known in the art. For instance, DNA sequences may be synthesized by phosphoamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing greater than about 50%, most preferably at least about 80%, of the codons to host-preferred codons. The codon preferences of many host cells are known. See, e.g., *Maximizing Gene Expression*, pages 225-85 (Reznikoff & Gold, eds., 1986), PCT WO 97/31115, PCT WO 97/11086, EP 646643, EP 553494, and U.S. Pat. Nos. 5,689,052, 5,567,862, 5,567,600, 5,552,299 and 5,017,692. The codon preferences of other host cells can be deduced by methods known in the art. Also, using chemical synthesis, the sequence of the DNA molecule or its encoded protein can be readily changed to, e.g., optimize expression (e.g., eliminate mRNA secondary structures that interfere with transcription or translation), add unique restriction sites at convenient points, delete protease cleavage sites, etc.

In a third embodiment, the present invention provides DNA constructs comprising DNA coding for a dicamba-degrading enzyme operatively linked to expression control sequences or a plurality of DNA coding sequences, each coding for a dicamba-degrading enzyme and each being operatively linked to expression control sequences. "DNA constructs" are defined herein to be constructed (non-naturally occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded proteins are expressed.

Methods of operatively linking expression control sequences to coding sequences are well known in the art. See, e.g., Maniatis et al., *Molecular Cloning: A Laboratory Manual*, Cold Spring Harbor, NY (1982), Sambrook et al., *Molecular Cloning: A Laboratory Manual*, Cold Spring Harbor, NY (1989).

"Expression control sequences" are DNA sequences involved in any way in the control of transcription or translation in prokaryotes and eukaryotes. Suitable expression control sequences and methods of making and using them are well known in the art.

The expression control sequences must include a promoter. The promoter may be any DNA sequence which shows transcriptional activity in the chosen host cell or organism. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, *Nucleic Acids Res.*, 15, 2343-61 (1987). Also, the location of the promoter relative to the transcription start may be optimized. See, e.g., Roberts, et al., *Proc. Natl Acad. Sci. USA*, 76, 760-4 (1979). Many suitable promoters for use in prokaryotes and eukaryotes are well known in the art.

For instance, suitable constitutive promoters for use in plants include: the promoters from plant viruses, such as the 35S promoter from cauliflower mosaic virus (Odell et al., *Nature* 313:810-812 (1985), promoters of Chlorella virus methyltransferase genes (U.S. Pat. No. 5,563,328), and the full-length transcript promoter from figwort mosaic virus (U.S. Pat. No. 5,378,619); the promoters from such genes as rice actin (McElroy et al., *Plant Cell* 2:163-171 (1990)), ubiquitin (Christensen et al., *Plant Mol. Biol.* 12:619-632 (1989) and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genet.* 231:276-285 (1992) and Atanassova et al., *Plant Journal* 2(3):291-300 (1992)), *Brassica napus* ALS3 (PCT application WO 97/41228); and 11 promoters of various *Agrobacterium* genes (see U.S. Pat. Nos. 4,771,002, 5,102,796, 5,182,200, 5,428,147).

Suitable inducible promoters for use in plants include: the promoter from the ACEI system which responds to copper (Mett et al. *PNAS* 90:4567-4571 (1993)); the promoter of the maize In2 gene which responds to benzenesulfonamide herbicide safeners (Hershey et al., *Mol. Gen. Genetics* 227:229-237 (1991) and Gatz et al., *Mol. Gen. Genetics* 243:32-38 (1994)), and the promoter of the Tet repressor from Tn10 (Gatz et al., *Mol. Gen. Genet* 227:229-237(1991). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone. Schena et al., *Proc. NatL. Acad Sci. USA* 88:10421 (1991). Other inducible promoters for use in plants are described in EP 332104, PCT WO 93/21334 and PCT WO 97/06269.

Suitable promoters for use in bacteria include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gene, the *Bacillus pumilus* xylosidase gene, the phage lambda $P_R$ and $P_L$ promoters, and the *Escherichia coli* lac, trp and tac promoters. See PCT WO 96/23898 and PCT WO 97/42320.

Suitable promoters for use in yeast host cells include promoters from yeast glycolytic genes, promoters from alcohol dehydrogenase genes, the TPII promoter, and the ADH2-4c promoter. See PCT WO 96/23898.

Suitable promoters for use in filamentous fungi include the ADH3 promoter, the tpiA promoter, the promoters of the genes encoding Aspergillus oryzae TAKA amylase, *Rhizomucor miehei* aspartic proteinase, *Aspergillus niger* neutral alpha-amylase, *A. niger* acid stable alpha-amylase, *A. niger* or *Aspergillus awamori* glucoamylase, *R. miehei* lipase, *A. oryzae* alkaline protease, *A. oryzae* triose phosphate isomerase, and *Aspergillus nidulans* acetamidase. See PCT WO 96/23898.

Suitable promoters for use in mammalian cells are the SV40 promoter, metallothionein gene promoter, murine mammary tumor virus promoter, Rous sarcoma virus promoter, and adenovirus 2 major late promoter. See PCT WO 96/23898 and PCT WO 97/42320.

Suitable promoters for use in insect cells include the polyhedrin promoter, P10 promoter, the *Autographa californica* polyhedrosis virus basic protein promoter, the baculovirus immediate early gene 1 promoter and the baculovirus 39K delayed-early gene promoter. See PCT WO 96/23898.

Finally, promoters composed of portions of other promoters and partially or totally synthetic promoters can be used. See, e.g.,Ni et al., *Plant J*, 7:661-676 (1995)and PCT WO 95/14098 describing such promoters for use in plants.

The promoter may include, or be modified to include, one or more enhancer elements.

Preferably, the promoter will include a plurality of enhancer elements. Promoters containing enhancer elements provide for higher levels of transcription as compared to promoters which do not include them. Suitable enhancer elements for use in plants include the 35S enhancer element from cauliflower mosaic virus (U.S. Pat. Nos. 5,106,739 and 5,164,316) and the enhancer element from figwort mosaic virus (Maiti et al., *Transgenic Res.*, 6, 143-156 (1997)). Other suitable enhancers for use in other cells are known. See PCT WO 96/23898 and *Enhancers And Eukaryotic Expression* (Cold Spring Harbor Press, Cold Spring Harbor, NY, 1983).

For efficient expression, the coding sequences are preferably also operatively linked to a 3' untranslated sequence. The 3' untranslated sequence contains transcription and/or translation termination sequences. The 3' untranslated regions can be obtained from the flanking regions of genes from bacterial, plant or other eukaryotic cells. For use in prokaryotes, the 3' untranslated region will include a transcription termination sequence. For use in plants and other eukaryotes, the 3' untranslated region will include a transcription termination sequence and a polyadenylation sequence. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

In plants and other eukaryotes, a 5' untranslated sequence is also employed. The 5' untranslated sequence is the portion of an mRNA which extends from the 5° CAP site to the translation initiation codon. This region of the mRNA is necessary for translation initiation in eukaryotes and plays a role in the regulation of gene expression. Suitable 5' untranslated regions for use in plants include those of alfalfa mosaic virus, cucumber mosaic virus coat protein gene, and tobacco mosaic virus.

As noted above, the DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the sequences coding for the dicamba-degrading enzymes of the invention. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform a variety of host cells (see below). A genetic marker must be used for selecting transformed host cells ("a selection marker"). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant regulatory signals, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford et al., *Plant Physiol.* 86:1216 (1988), Jones et al., *Mol. Gen. Genet.* 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Commonly used genes for screening presumptively transformed cells include β-glucuronidase (GUS), β-galactosidase, luciferase, and chloramphenicol acetyltransferase. Jefferson, R. A., *Plant Mol. Biol. Rep.* 5:387 (1987)., Teeri et al., *EMBO J.* 8:343 (1989), Koncz et al., *Proc. Natl. Acad. Sci. USA* 84:131 (1987), De Block et al., *EMBO J.* 3:1681 (1984), green fluorescent protein (GFP) (Chalfie et al., *Science* 263: 802 (1994), Haseloff et al., *TIG* 11:328-329 (1995) and PCT application WO 97/41228). Another approach to the identification of relatively rare transformation events has been use of a gene that encodes a dominant constitutive regulator of the *Zea mays* anthocyanin pigmentation pathway. Ludwig et al., *Science* 247:449 (1990).

Suitable selection markers for use in prokaryotes and eukaryotes other than plants are also well known. See, e.g., PCT WO 96/23898 and PCT WO 97/42320. For instance, resistance to antibiotics (ampicillin, kanamycin, tetracyline, chloramphenicol, neomycin or hygromycin) may be used as the selection marker.

According to another aspect of the present invention, tolerance to dicamba can be used as a selection marker for plants and plant cells. "Tolerance" means that transformed plant cells are able to grow (survive and regenerate into plants) when placed in culture medium containing a level of dicamba that prevents untransformed cells from doing so. "Tolerance" also means that transformed plants are able to grow after application of an amount of dicamba that inhibits the growth of untransformed plants.

Methods of selecting transformed plant cells are well known in the art. Briefly, at least some of the plant cells in a population of plant cells (e.g., an explant or an embryonic suspension culture) are transformed with a DNA construct or combination of DNA constructs providing for dicamba degradation. The resulting population of plant cells is placed in culture medium containing dicamba at a concentration selected so that transformed plant cells will grow, whereas untransformed plant cells will not. Suitable concentrations of dicamba can be determined empirically as is known in the art.

Methods of selecting transformed plants are also known in the art. Briefly, dicamba is applied to a population of plants suspected of comprising a DNA construct or a combination of DNA constructs providing for dicamba degradation. The amount of dicamba is selected so that transformed plants will grow, and the growth of untransformed plants will be inhibited. The level of inhibition must be sufficient so that transformed and untransformed plants can be readily distinguished (i.e., inhibition must be statistically significant). Such amounts can be determined empirically as is known in the art.

Further, the generation of 3,6-DCSA as a result of the degradation of dicamba can be used for selection and screening. The generation of 3,6-DCSA can be readily ascertained by observing the fluorescence of this compound, allowing selection and screening of transformed host cells, intact organisms, and parts of organisms (e.g., microorganisms, plants, plant parts, and plant cells). In this regard, the invention allows for selection and screening of transformed host cells, intact organisms, and parts of organisms in the same manner as for green fluorescent protein (GFP). See U.S. Pat. Nos. 5,162,227 and 5,491,084 and PCT applications WO 96/27675, WO 97/11094, WO 97/41228 and WO 97/42320, all of which are incorporated herein by reference. In particular, 3,6-DCSA can be detected in transformed host cells, intact organisms, and parts of organisms using conventional spectrophotometric methods. For instance, microscopes can be fitted with appropriate filter combinations for fluorescence excitation and detection. A hand-held lamp may be used for benchtop work or field work (see Example 1). Fluorescence-activated cell sorting can also be employed. 3,6-DCSA is excited at a wavelength of 312-313 nm, with a maximum emission wavelength of 424 nm.

"Parts" of organisms include organs, tissues, or any other part. "Plant parts" include seeds, pollen, embryos, flowers, fruits, shoots, leaves, roots, stems, explants, etc.

Selection based on dicamba tolerance or dicamba degradation can be used in the production of dicamba-tolerant plants or dicamba-degrading microorganisms, in which case the use of another selection marker may not be necessary. Selection based on dicamba tolerance or dicamba degradation can also be used in the production of transgenic cells or organisms that express other genes of interest. Many such genes are known and include genes coding for proteins of commercial value and genes that confer improved agronomic traits on plants (see, e.g., PCT WO 97/41228, the complete disclosure of which is incorporated herein by reference).

The DNA constructs of the invention can be used to transform a variety of host cells, including prokaryotes and eukaryotes. The DNA sequences coding for the dicamba-degrading enzyme(s) and the selection marker, if a separate selection marker is used, may be on the same or different DNA constructs. Preferably, they are arranged on a single DNA construct as a transcription unit so that all of the coding sequences are expressed together. Also, the gene(s) of interest and the DNA sequence(s) coding for the dicamba-degrading enzyme(s), when dicamba-tolerance or dicamba degradation is being used as a selection marker, may be on the same or different DNA constructs. Such constructs are prepared in the same manner as described above.

Suitable host cells include prokaryotic and eukaryotic microorganisms (e.g., bacteria (including *Agrobacterium tumefaciens* and *Escherichia coli*), yeast (including *Saccharomyces cerevisiae*) and other fungi (including *Aspergillus* sp.), plant cells, insect cells, and mammalian cells. Preferably, the host cell is one that does not normally degrade dicamba. However, the present invention can also be used to increase the level of dicamba degradation in host cells that normally degrade dicamba.

Thus, the "transgenic" cells and organisms of the invention include cells and organisms that do not normally degrade dicamba, but which have been transformed according to the invention so that they are able to degrade this herbicide. The "transgenic" cells and organisms of the invention also include cells and organisms that normally degrade dicamba, but which have been transformed according to the invention so that they are able to degrade more of this herbicide or to degrade the herbicide more efficiently.

Methods of transforming prokaryotic and eukaryotic host cells are well known in the art. See, e.g., Maniatis et al., *Molecular Cloning: A Laboratory Manual*, Cold Spring Harbor, NY (1982), Sambrook et al., *Molecular Cloning: A Laboratory Manual*, Cold Spring Harbor, NY (1989); PCT WO 96/23898 and PCT WO 97/42320.

For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B.R. and Thompson, J.E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B.R. and Thompson, J.E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

Transgenic dicamba-tolerant plants of any type may be produced according to the 20. invention. In particular, broadleaf plants (including beans, soybeans, cotton, peas, potatoes, sunflowers, tomatoes, tobacco, fruit trees, and ornamental plants and trees) that are currently known to be injured by dicamba can be transformed so that they become tolerant to the herbicide. Other plants (such as corn, sorghum, small grains, sugarcane, asparagus, and grass) which are currently considered tolerant to dicamba can be transformed to increase their tolerance to the herbicide. "Tolerant" means that the transformed plants can grow in the presence of an amount of dicamba which inhibits the growth of untransformed plants It is anticipated that the dicamba-degrading oxygenases of the invention can function with endogenous reductases and ferredoxins found in transgenic host cells and organisms to degrade dicamba. Plant chloroplasts are particularly rich in reductases and ferredoxins. Accordingly, a preferred embodiment for the production of transgenic dicamba-tolerant plants is the use of a sequence coding for a peptide that will direct the dicamba-degrading oxygenase into chloroplasts ("a chloroplast targeting sequence"). DNA coding for the chloroplast targeting sequence is preferably placed upstream (5') of the sequence coding for the dicamba-degrading oxygenase, but may also be placed downstream (3') of the coding sequence, or both upstream and downstream of the coding sequence. Exemplary chloroplast targeting sequences include the maize cab-m7 signal sequence (see Becker et al., *Plant Mol. Biol.* 20:49 (1992) and PCT WO 97/41228) and the pea glutathione reductase signal sequence (Creissen et al., *Plant J* 2:129 (1991) and PCT WO 97/41228). An alternative preferred embodiment is the direct transformation of chloroplasts using a construct comprising a promoter functional in chloroplasts to obtain expression of the oxygenase in chloroplasts. See, e.g., PCT application WO 95/24492 and U.S. Pat. No. 5,545, 818. Of course, if a selected transgenic host cell or organism does not produce sufficient endogenous reductase, ferredoxin, or both, the host cell or organism can be transformed so that it produces one or both of these enzymes as well as the oxygenase.

In yet another embodiment, the invention provides a method of controlling weeds in a field where transgenic dicamba-tolerant plants are growing. The method comprises applying an effective amount of dicamba to the field to control the weeds. Methods of applying dicamba and amounts of dicamba effective to control various types of weeds are known. See *Crop Protection Reference*, pages 1803-1821 (Chemical & Pharmaceutical Press, Inc., New York, N.Y., 11th ed., 1995).

In another embodiment, the invention provides a method of degrading dicamba present in a material, such as soil, water, or waste products of a dicamba manufacturing facility. Such degradation can be accomplished using the dicamba-degrading enzymes of the invention. The enzymes can be purified from microorganisms naturally expressing them (see Examples 1 and 3) or can be purified from transgenic host cells producing them. If the enzymes are used in such methods, then appropriate cofactors must also be provided (see Example 1). Effective amounts can be determined empirically as is known in the art (see Example 1). Alternatively, transgenic prokaryotic and eukaryotic microorganisms can be used to degrade dicamba in such materials. Transgenic prokaryotic and eukaryotic microorganisms can be produced as described above, and effective amounts can be determined empirically as is known in the art.

Dicamba is introduced into the environment in large quantities on a continuing basis. The elimination of dicamba is dependent in large part on the action of enzyme systems which are found in microorganisms inhabiting the soil and water of the planet. An understanding of these enzyme systems, including dicamba-degrading O-demethylases and their three components, is important in efforts to exploit natural and genetically modified microbes for bioremediation and the restoration of contaminated soil, water and other materials. Thus, the dicamba-degrading enzymes, DNA molecules, DNA constructs, etc., of the invention can be used as research tools for the study of dicamba degradation and bioremediation.

Finally, the dicamba-degrading enzymes of the invention can be used in an assay for dicamba. A sample suspected of containing dicamba is mixed with a dicamba-degrading O-demethylase or a combination of a dicamba-degrading oxygenase, a dicamba-degrading ferredoxin and a dicamba-degrading reductase. Suitable assays are described in Examples 1 and 3. In particular, detecting or quantitating the fluorescence due to the generation of 3,6-DCSA makes for a convenient assay.

EXAMPLES

Example 1

Purification And Characterization Of The Components Of Dicamba O-Demethylase Of *Pseudomonas maltophilia* DI-6

METHODS AND MATERIALS

Bacterium and growth conditions. *Pseudomonas maltophilia*, strain DI-6 (Kreuger, et al., (1 989) *J. Agric. Food Chem.*, 37:534-538) was isolated from a soil site persistently contaminated with dicamba. The bacterium was provided by Dr. Douglas Cork of the Illinois Institute of Technology (Chicago, Ill.), and was maintained on reduced chloride medium (Kreuger, J. P., (1989) Ph.D. thesis, Illinois Institute of Technology, Chicago, Ill.), supplemented with either dicamba (2 mg/ml) or a mixture of glucose (2 mg/ml) and Casamino Acids (2 mg/ml). The carbon sources were filter-sterilized and added to the medium after it was autoclaved. Solid media were prepared by the addition of 1% (wt/vol) Gelrite (Scott Laboratories, West Warwick, R.I.).

Chemicals and reagents. Dicamba, 3,6-DCSA, and [$^{14}$C] dicamba (U-phenyl-$^{14}$C, 42.4 mCi/mmol, radiochemical purity greater than 98%) were supplied by Sandoz Agro, Inc. (Des Plaines, Ill.). To increase solubility, the dicamba and 3,6-DCSA stock solutions were prepared by titration with KOH to pH 7.0. All chemicals were purchased from Sigma Chemical Co. (St. Louis, Mo.), unless otherwise stated. Superose 12, Mono Q, Q-Sepharose (Fast Flow) and Phenyl-Sepharose (CL-4B) column packings for the FPLC (fast performance liquid chromatography) apparatus were obtained from Pharmacia (Milwaukee, Wis.). Ampholyte pH 4-6 and ampholyte pH 4-9 were purchased from Serva (Heidelberg, FRG). Acrylamide, β-mercaptoethanol, N,N,N',N'-tetramethylethylenediamine (TEMED) and ammonium persulfate (APS) were from Bio-Rad Laboratories (Hercules, Calif.). Thin layer chromatography (TLC) plates were silica gel (250 μm thickness) with UV 254 indicator, and were purchased from J. T. Baker Chemical Co. (Phillipsburg, N.J.).

Enzyme assays. Dicamba O-demethylase activity was assayed by measuring the formation of [$^{14}$C]3,6-DCSA from [$^{14}$C]dicamba. Briefly, the activity in mixtures of enzyme components was measured at 30° C. in a standard 300 μl reaction mixture containing 25 mM potassium phosphate buffer (pH 7.0), 10 mM $MgCl_2$, 0.5 mM NADH (beta-nicotinamide adenine dinucleotide, reduced form), 0.5 mM ferrous sulfate, 50 μM cold dicamba, 2.5 μM [$^{14}$C] dicamba (the final specific activity of the radioactive dicamba was 1.9 mCi/mmol), and different amounts of cell lysate or partially purified enzyme. All enzyme assays during the final purification steps were conducted in phosphate buffer because the pH optimum for. dicamba O-demethylase activity was found to be in the mid range of phosphate buffers, and higher enzyme activity was observed with phosphate buffer compared to Tris-HCl [tris(hydroxymethyl)aminomethane hydrochloride] buffer at pH 7.0. Reactions were initiated by the addition of the substrate, dicamba. At specific times, the reactions were stopped by adding 50 μl of 5% (vol/vol) $H_2SO_4$. Dicamba and dicamba metabolites were then extracted twice with one volume of ether, and the extracts were evaporated to dryness. The efficiencies of recovery (means ±standard deviations) for the extraction procedure were 87% ±2% for dicamba and 85% ±3% for 3,6-DCSA (Yang et al., *Anal. Biochem.* 219:37-42 (1994)).

[$^{14}$C]dicamba and $^{14}$C-labeled metabolites were separated by thin layer chromatography (TLC). The ether-extracted dicamba and its metabolites were redissolved in 50 μl of ether prior to being spotted onto a TLC plate. The solvent system for running the TLC was chloroform-ethanol-acetic acid (85: 10:5 [vol/vol/vol]). The resolved reaction products were visualized and quantified by exposing the TLC plate to a phosphor screen for 24 hours and then scanning the screen in a PhosphorImager SF (Molecular Dynamics, Sunnyvale, Calif.). Estimates of the amount of radioactivity in a particular spot on the TLC plate were determined by comparing the total pixel count in that spot relative to a spot on the same plate containing a known amount of [$^{14}$C]dicamba. One unit of activity was defined as the amount of enzyme that catalyzes the formation of 1 nmol of 3,6-DCSA from dicamba per minute at 30° C. Specific activities were based on the total protein concentration of the assay mixture.

The activity of the reductase component of dicamba demethylase was assayed by measuring reduction of 2,6-dichlorophenolindophenol (DCIP) with a Hitachi U-2000 spectrophotometer. The reaction contained 0.5 mM NADH, 0.2 mM FAD (flavin adenine dinucleotide), 50 µM DCIP, 20 mM Tris buffer (pH 8.0), and 10-100 µl of enzyme sample in a total volume of 1 ml. The change in absorbance at 600 nm with time was measured at room temperature. Specific activity was calculated using an extinction coefficient at 600 nm of 2 1.0 $mM^{-1}cm^{-1}$ for reduced DCIP. Specific activity was expressed as nmol DCIP reduced $min^{-1}$ $mg^{-1}$ of protein.

In addition, an in situ DCIP assay was used to detect and locate the reductase activity in protein preparations separated on isoelectric focusing (IEF) gels. After electrophoresis of the proteins on an IEF gel, lanes sliced from the gel were washed with 20 ml of cold 20 mM Tris-HCl buffer (pH 8.0). Low melting agarose was dissolved by heating in 10 ml of 20 mM Tris-HCl buffer (pH 8.0) at a final concentration of 1.5% (w/v). When the agarose cooled to near room temperature, it was supplemented with 0.2 mM FAD, 50 µM DCIP, and 0.5 mM NADH. The assay mixture was poured onto a glass plate and allowed to solidify. The gel piece was placed on top of the solidified reaction mixture and allowed to set at room temperature for 15 minutes. If the gel slice contained a protein with reductase activity, a colorless band of reduced DCIP was generated in the blue background of DCIP.

Cell lysates. Cells were grown to an optical density at 550 nm of 1.3 to 1.5 in liquid reduced chloride medium containing a mixture of glucose and Casamino Acids on a rotary shaker (250 rpm at 30° C.). The cells were harvested by centrifugation, washed twice with cold 100 mM $MgCl_2$, and centrifuged again. Cell pastes were either used immediately or quickly frozen in liquid nitrogen and stored at −80° C. At the time of enzyme purification, 25 g of frozen cells were thawed and resuspended in 50 ml of isolation buffer containing 25 mM Tris buffer (pH 7.0), 10 mM $MgCl_2$, and 0.5 mM EDTA. Phenylmethylsulfonyl fluoride and dithiothreitol were added to final concentrations of 0.5 mM and 1 mM, respectively. After addition of 10 mg of lysozyme and 1 mg of DNase, cells were stirred for 10 min on ice and broken by sonication (model XL2020 sonicator; Heat Systems) on ice at a medium setting (setting 5) with twelve 20-second bursts and 40-second resting intervals. The resulting cell lysates were diluted to 90 ml with isolation buffer and centrifuged at 76,000×g for 1 h at 4° C. The supernatant was used as the source of cleared cell lysate.

Enzyme purification. All procedures were performed at 4° C., unless otherwise stated. Solid ammonium sulfate was slowly added to a 90-ml volume of cleared cell lysate to 40% (wt/vol) saturation, with constant stirring. After 15 minutes of stirring, the mixtures were centrifuged at 15,400×g for 15 minutes, and the precipitate was discarded. Additional solid ammonium sulfate was added to 70% (wt/vol) saturation, with constant stirring of the supernatant. After 15 min of stirring, the mixtures were centrifuged under the conditions described above. The supernatant was discarded, and the precipitate was resuspended in a minimal volume of buffer A (20 mM Tris [pH 8.0], 2.5 MM $MgCl_2$, 0.5 mM EDTA, 5% (vol/vol) glycerol, and 1 mM dithiothreitol).

The 40%-70% ammonium sulfate cut was then loaded onto a Phenyl-Sepharose column (2.5 by 10 cm) connected to a FPLC apparatus (Pharmacia) and eluted with a decreasing linear gradient of $(NH_4)_2SO_4$ from 10% (w/v) to 0% (w/v). The column was preequilibrated with buffer A containing 10% (wt/vol) ammonium sulfate. The flow rate was 1 ml/min. Protein concentrations were continuous lymonitored at $A_{280}$ during column elution. The column was washed with 120 ml of buffer A containing 10% (wt/vol) ammonium sulfate until baseline $A_{280}$ readings were obtained. Bound proteins were eluted with a decreasing gradient of $(NH_4)_2SO_4$ in buffer A [10 to 0% (wt/vol) $(NH_4)_2SO_4$ in a total volume of 210 ml]. Fractions of 2 ml were collected. Aliquots of 10 µl were taken from each fraction and added to the standard dicamba O-demethylase assay mixture (see above), except that nonradioactive dicamba was used as the substrate. Dicamba O-demethylase activity was detected by monitoring the conversion of dicamba to the highly fluorescent reaction product 3,6-DCSA with a hand-held UV lamp (312 nm, Fotodyne) in a darkened room.

This procedure allowed resolution of dicamba O-demethylase into three pools containing the separated components (designated components I, II and III). Each component was essential for dicamba O-demethylase activity (see below). When a single component was assayed, the other two components were provided in excess. Fractions containing a single type of activity were pooled (component I, fractions 128-145; component II, unbound fractions 12-33; component III, fractions 62-92).

(i) Purification of component I. Fractions containing component I activity (eluting from a Phenyl-Sepharose column at 0 M $(NH_4)_2SO_4$, fractions 128-145) were pooled to provide a total volume of 34 ml. The pooled samples were concentrated to 10 ml by centrifugation in a Centriprep-10 device (Amicon) and then applied to a Q-Sepharose (Fast Flow) FPLC column (Pharmacia) (2.5 by 6 cm) equilibrated with buffer A and washed with 80 ml of buffer A. Proteins bound to the column were eluted with a 100 ml linear gradient of 0 to 0.6 M KCl in buffer A at a flow rate of 1 ml/min. Fractions were collected at 1.5 minute intervals. Those fractions exhibiting component I activity (fractions 29-37) were pooled, dialyzed against buffer A overnight at 4° C. and applied to a Mono Q HR 5/5 FPLC anion-exchange column in buffer A. Proteins were eluted at 1 ml/min by using a 50 ml gradient of increasing KCl concentration (0 to 0.5 M). Fractions showing component I activity (fractions 19 to 25) were pooled and concentrated to 0.4 ml by centrifugation in a Centricon-10 device. The concentrated sample was then subjected to chromatography on a Superose 12 FPLC column (1.6 by 50 cm) at a flow rate of 0.2 ml/min with buffer A containing 100 mM KCl. Fractions 7-10 showing component I activity were pooled and concentrated by centrifugation in a Centricon-10 device.

The partially purified component I was diluted with cold 1% (w/v) glycine and concentrated by centrifugation in a Centricon-10 device three more times to desalt it in preparation for IEF electrophoresis. The desalted and concentrated sample was then applied to a 6% (w/v) IEF (pH 4-6) gel and subjected to electrophoresis for 1.5 hours at 4° C. (see below). After electrophoresis, the gel was washed with 25 mM cold phosphate buffer (pH 7.0) for 5 minutes and then each slice of the gel lane was diced into small (6 mm×4 mm) pieces. Protein was eluted from the diced gel fragments by grinding them with a pipette tip in the presence of 10 µl of 25 mM phosphate buffer (pH 7.0). Protein from each segment was mixed with an excess of components II and III and assayed for dicamba O-demethylase activity. The gel segment which showed component I activity (which was also reddish brown in color) was loaded onto a 12.5% (w/v) sodium dodecyl sulfate polyacrylamide gel (SDS-PAGE) to check sample purity.

(ii) Purification of component II. Component II obtained by Phenyl-Sepharose column chromatography was dialyzed against buffer A overnight at 4° C. and applied to a FPLC Q-Sepharose column (2.5 by 6 cm). Sample elution conditions were identical to those described above for component I except that the elution gradient was 0 to 1 M KCl in buffer A. Fractions exhibiting component II activity (fractions 30-37) were pooled, dialyzed against buffer A, concentrated to 0.4 ml and applied to a FPLC Superose 12 column (1.6 by 50 cm). The procedures for sample application and elution were identical to those described above for component I. Fractions exhibiting component II activity (fractions 3-6) were pooled, diluted with an equal volume of buffer A, and applied to a FPLC Mono Q column. Proteins were eluted from the column using the same KCl gradient as for component I. Fractions 20-25 showed component II activity. Partially purified component II was further purified by IEF (pH 4-6) electrophoresis using the same conditions as described for component I. The gel segment which showed component II activity was loaded onto a 12.5% (w/v) SDS-PAGE for further analysis.

(iii) Purification of component III. Component III obtained by Phenyl-Sepharose column chromatography was dialyzed against buffer A overnight at 4° C. and applied to a FPLC Q-Sepharose column (2.5 by 6 cm). Conditions were identical to those described above for component I. Fractions exhibiting component III activity (fractions 26-38) were dialyzed against buffer B [10 mM Tris-HCl (pH 7.5), 2.5 mM $MgCl_2$, 5% (v/v) glycerol, l mM dithiothreitol] and concentrated to 5 ml. Blue dye affinity matrix [Cibacron Blue 3GA type 3000 (Sigma)] was packed into a FPLC column (1×5 cm) and pre-equilibrated with 20 ml of buffer B. Concentrated component III was loaded onto the blue dye column and washed with 20 ml of buffer B at a flow rate of 0.2 ml/min until the $A_{280}$ of the column effluent reached baseline levels. Bound protein was then eluted with 5 mM NADH in buffer B. Fractions containing reductase activity were detected by assaying for dicamba O-demethylase activity in the presence of an excess of components I and II and also by the ability of each fraction to reduce DCIP in the presence of NADH. Fractions having strong reductase activity in both assays were pooled, dialyzed against buffer A containing 100 mM KCl, concentrated to 0.2 ml, and applied to a FPLC Superose 12 column. The same conditions were used for running the Superose column as described for component I. Fractions containing proteins which catalyzed DCIP reduction were pooled, dialyzed against buffer A and applied to a FPLC Mono Q column. Proteins were eluted using the same conditions as for component I. Partially purified component III was further purified by IEF (pH 4-6) gel electrophoresis. The reductase activity of proteins within the IEF gel was detected by assaying for DCIP reduction in an agarose gel overlay as described above. The gel segment which showed component II activity was loaded onto a 12.5% (w/v) SDS-PAGE for further analysis.

Determination of $NH_2$-terminal amino acid sequences. Protein bands were excised from IEF gels and placed in the wells of a 12.5% (w/v) SDS polyacrylamide gel. After electrophoresis, the gel slices containing the purified proteins were transblotted onto a PVDF (polyvinylidene difluoride) membrane (Millipore) in a Trans-Blot cell (Bio-Rad, Richmond, Calif.) at 25 volts for 16 hours. The blotting buffer was a solution of 20% (v/v) methanol with 10 mM CAPS [3-(cyclohexylamino)-1-propanesulfonic acid], pH 10.0. Sequencing was performed using an Applied Biosystems Inc. 420 H machine by Edman degradation (Edman 20 and Henschen (1975) pages 232-279 in S.B. Needleman (ed.), Protein sequence determination, 2nd ed., Springer-Verlage, New York).

Determination of protein concentration. Protein concentrations were determined by the method of Bradford (1976) AnaL Biochem. 72:248-254, with bovine serum albumin as the standard.

SDS-PAGE. Sodium dodecyl sulfate-polyacrylamide gel eletrophoresis (SDS-PAGE) was performed according to modified methods of Laemmli (Laemmli (1970) *Nature,* 227: 680-685). 12.5% (w/v) SDS gels of 85×65×0.75 mm were made as follows: running gel: 2.5 ml 40% (w/v) acrylamide/bis solution (37:5:1), 1 ml running buffer solution [3M Tris-HCl (pH 8.8), 0.8% (w/v) SDS], 4.5 ml $H_2O$, 5 µl TEMED, and 40 µl 10% (w/v) APS; stacking gel: 0.5 ml 40% (w/v) acrylamide/bis, 0.5 ml stacking buffer solution [1 M Tris-HCl (pH 6.8), 0.8% (w/v) SDS], 3 ml $H_2O$, 5 µl TEMED, and 12.5 µl 10% (w/v) APS. The composition of the running buffer was 25 mM Tris-HCl (pH 8.3), 0.2 M glycine, and 0.1 % (w/v) SDS. The sample buffer contained 0.25 ml stacking buffer, 0.6 ml 20% (w/v) SDS, 0.2 ml β-mercaptoethanol, and 0.95 ml 0.1 % bromphenol blue (w/v) in 50% (v/v) glycerol. Electrophoresis was performed at 80 volts in a Bio-Rad Mini Gel apparatus until the tracking dye was 0.5 cm from the anode end of the gel. Proteins were stained with 0.1% (w/v) Coomassie Brilliant Blue R-250 in a mixture of isopropanol, water, and acetic acid at a ratio of 3:6:1 (v/v/v). Destaining was performed in a mixture of methanol, water, and acetic acid at a ratio of 7:83:10 (v/v/v). Standard proteins (Gibco BRL) included: myosin (214.2 kDa), phosphorylase B (111.4 kDa), bovine serum albumin (74.25 kDa), ovalbumin (45.5 kDa), carbonic anhydrase (29.5 kDa), β-lactoglobulin (18.3 kDa), and lysozyme (15.4 kDa).

Determination of molecular weight. The molecular weight ($M_r$) of peptides under denaturing conditions was estimated using SDS-PAGE analysis. The molecular weights of the native components 1, 11 and III were estimated by gel filtration through a Superose 12 HR 10/30 FPLC column (Pharmacia) at a flow rate of 0.2 ml/min in buffer A containing 100 mM KCl. Calibration proteins were gel filtration standards from Bio-Rad. They were: bovine thyroglobulin (670 kDa), bovine gamma globulin (158 kDa), chicken ovalbumin (44 kDa), horse myoglobin (17 kDa) and vitamin B- 12 (1.35 kDa). The void volume of the Superose 12 column was calculated using Blue Dextran ($M_r$ 2,000,000, Sigma).

IEF. Isoelectric focusing (IEF) gel electrophoresis was performed in a vertical mini-gel apparatus (Model #MGV-100) from C.B.S. Scientific Co. (Del Mar, Calif.). IEF gels with 6% (w/v) polyacrylamide (70 x 90 x 1 mm) were made by mixing the following: 1.6 ml 30% (w/v) acrylamide/bis (37:5:1), 0.8 g glycerol, 0.32 ml ampholyte pH 4-6 (Serva), 0.08 ml ampholyte pH 4-9 (Serva), 5.2 ml $H_2O$, 10 µl TEMED, and 80 µl 10% (w/v) APS. The cathode buffer was 100 mM β-alanine and the anode buffer was 100 mM acetic acid. Protein samples in approximately 1 to 10 µl of 1% (w/v) glycine were mixed with an equal volume of sample buffer [50% (v/v) glycerol, 1.6% (v/v) ampholyte pH 4-9, 2.4% (v/v) ampholyte pH 4-6]. Samples were loaded at the cathode end of the gel and allowed to migrate at 200 volts for 1.5 hours and 400 volts for another 1.5 hours. Proteins were stained with Coomassie Brilliant Blue R-250 using the procedure described above for SDS polyacrylamide gels. IEF markers (Sigma) were: amyloglucosodase, pI 3.6; glucose oxidase, pI 4.2; trypsin inhibitor, pI 4.6; β-lactoglobulin A, pI 5.1; carbonic anhydrase II, pI 5.4; carbonic anhydrase II, pI 5.9 and carbonic anhydrase I, pI 6.6

Kinetic analysis. The kinetics of the demethylation reaction catalyzed by dicamba O-demethylase were studied by analyzing the initial rates of the reaction in the presence of a constant concentration of the enzyme and increasing concentrations of the substrate, dicamba. Reaction mixtures contained 25 mM potassium phosphate buffer (pH 7.0), 10 mM $MgCl_2$, 0.5 mM NADH, 0.5 mM $FeSO_4$, 25 µg of partially purified O-demethylase enzyme [the 40%-70% (w/v) $(NH_4)_2SO_4$ fraction from a cleared cell lysate], various concentrations (0.5 to 50 µM) of dicamba and various concentrations (0.025 to 2.5 µM) of [$^{14}$C]dicamba (U-phenyl-$^{14}$C, 42.4 mCi/mmol) in a total volume of 300 µl. For assays with dicamba concentrations of 0.5 µM and 1 µM, the reaction volume was increased to 900 µl to ensure that sufficient amounts of radioactive dicamba and its metabolites were present to allow detection. In these reactions, the amounts of all other components in the reaction were tripled. The conversion of [$^{14}$C]dicamba to [$^{14}$C]3,6-DCSA was determined for different time points at each concentration of dicamba using a PhosphorImager SF to scan radioactivity on phosphor screens which had been exposed to TLC plates for 24 hours. One unit of activity was defined as the amount of enzyme that forms 1 nmol of 3,6-DCSA per minute at 30° C. The initial rates of each reaction were determined by plotting the reaction rate versus time at each substrate concentration. Data were modeled to Michaelis-Menten kinetics and values of $K_m$ and $V_{max}$ were determined by fitting to Lineweaver-Burk plots using SigmaPlot® (Jandel Scientific, Corte Madera, Calif.).

Oxygen requirement. Preliminary experiments using a Clark oxygen electrode indicated oxygen consumption during a standard dicamba O-demethylase assay with dicamba as a substrate. To verify a requirement for oxygen in the 0 demethylation of dicamba by dicamba O-demethylase, reactions were conducted in an anaerobic chamber which contained less than 1 ppm of oxygen. The procedures for displacement of oxygen from the reaction mixture were performed at 4° C. Reaction mixtures lacking enzyme were placed in a vial and sealed with a rubber stopper. For displacement of oxygen, the vial was evacuated twice by vacuum and flushed each time with nitrogen. After a third evacuation, the vial was flushed with 90% nitrogen plus 10% hydrogen. The enzyme solution was likewise purged of oxygen (with care taken not to bubble the enzyme solution). Both the reaction mixtures and enzyme solutions were transferred into an anaerobic chamber (95% $N_2$-5% $H_2$ atmosphere). Two hundred forty microliters of cleared cell lysate was injected through the rubber stopper with a microsyringe and gently mixed with 960 µl of oxygen-free reaction mixture. Reactions were carried out at 30° C.

An examination of the reaction products on TLC plates showed that the rate of [$^{14}$C]3,6-DCSA production from [$^{14}$C]dicamba under anaerobic conditions was significantly lower than the rate of reactions with the same amount of enzyme under aerobic conditions. Under anaerobic conditions, there was virtually no conversion of dicamba to 3,6-DCSA within 1 hour. However, when a parallel reaction mixture was taken from the anaerobic chamber after 30 min and incubated with air, a significant quantity of one of the components of the dicamba O-demethylase enzyme complex was an oxygenase.

It may be noted that the in vitro conversion of [$^{14}$C]dicamba to [$^{14}$C]3,6-DCSA mimics the in vivo conversion pathway documented earlier (Cork and Kreuger, *Adv. Appl. Microbiol.* 36:1-66 (1991); Yang et al., *Anal. Biochem.* 219: 37-42(1994)). In these studies, DCSA was identified as a reaction product by both TLC and capillary electrophoresis. Stringent identification of the first major product of dicamba degradation as DCSA both in vivo and in vitro has been obtained by gas chromatography-mass spectrometry analyses.

Component and cofactor requirements. After the initial separation of the three components of dicamba O-demethylase by phenyl-Sepharose column chromatography, the partially purified preparations were taken individually through one additional purification on a Q-Sepharose column (2.5 by 6 cm). Samples were applied to a Q-Sepharose (Fast Flow) fast protein liquid chromatography column (Pharmacia) in buffer A and eluted with a 100-ml linear gradient of 0 to 0.6 M KCl (for the oxygenase component) or 0 to 1.0 M KCl (for the ferredoxin and reductase components) in 1.5-ml fractions. Appropriate pooled fractions from separate columns for oxygenase purification (fractions 29 to 37), for ferredoxin purification (fractions 30 to 37), or for reductase purification (fractions 26 to 38) were used for the determination of component and cofactor requirements.

The three components were assayed for O-demethylase activity in various combinations to determine component requirements.

To determine cofactor requirements, O-demethylase activity was assayed using a mixture of the three components with [$^{14}$C]dicamba for 30 minutes at 30° C. The amounts of partially purified protein (provided in an optimized ratio) in the reaction mixtures were 85 pg of oxygenase, 55 µg of ferredoxin and 50 µg of reductase. The concentration of cofactors used in the reaction mixtures were 0.5 mM NADH, 0.2 mM FAD, 0.5 mM $FeSO_4$, is 10 mM $MgCl_2$, 0.5 mM NADPH, and 0.2 mM FMN.

RESULTS

Component I. The component of dicamba O-demethylase which bound most tightly to the Phenyl-Sepharose column (designated initially as component I and subsequently identified as an oxygenase) was distinctly reddish brown in color. This indicated the potential presence of a protein(s) containing an iron-sulfur cluster(s) or aheme group(s). The fractions with component I activity from the Phenyl-Sepharose column were subjected to further purification by Q-Sepharose (Fast Flow) and Mono Q chromatography and then to separation on a Superose 12 size exclusion column. The component I protein was then further purified on an IEF gel.

Protein from the major band on the IEF gel (with an apparent pI of approximately 4.6) was excised and separated from any remaining minor contaminants by SDS-PAGE. The major component I protein obtained after purification by IEF was greater than 90% pure as judged by densitometric analysis of this SDS-polyacrylamide gel stained with Coomassie Blue. The N-terminal amino acid sequence of the dominant protein with an apparent molecular mass of approximately 40,000 Daltons was determined. Results of amino acid sequencing indicated that the first 29 amino acids of the N-terminal region were present in the following sequence (residues in parentheses are best guesses):

Thr Phe Val Arg Asn Ala Trp Tyr Val Ala Ala Leu Pro Glu Glu Leu Ser Glu Lys Pro Leu Gly Arg Thr Ile Leu Asp (Asp or Thr) (Pro) [SEQ ID NO:1].

Comparison with amino acid sequences in various databases indicated little or no homology with $NH_2$-terminal sequences reported for other monoxygenases or dioxygenases.

Component II. The protein fraction which did not bind to a Phenyl-Sepharose column was designated as component II. Because this yellowish colored fraction could be replaced by ferredoxin from *Clostridium pasteurianum* (but with slower reaction rates) when assays were performed in combination with components I and III, it was tentatively designated as a ferredoxin-containing fraction. The *Clostridium* ferredoxin clearly functioned in place of component II, but given the highly impure nature of the component II used in these experiments, the efficiency of the *Clostridium* enzyme was significantly lower than that of the putative ferredoxin from strain DI-6. In particular, 55 μg of partially purified component II mixed with excess amounts of components I and III catalyzed the conversion of dicamba to 3,6-DCSA at a rate of approximately 5 nmol min$^{-1}$ mg$^{-1}$, while 100 μg of highly purified ferredoxin from *Clostridium* resulted in an activity of only 0.6 nmol min$^{-1}$ mg$^{-1}$.

Purification steps involving Q-Sepharose (Fast Flow) chromatography, Superose 12 gel filtration and Mono Q chromatography yielded approximately one milligram of purified protein from an initial 25 grams of cell paste. This fraction was purified in a similar manner to the oxygenase component by electrophoresis on an IEF gel and subsequent electrophoresis of the active IEF fraction on an SDS-polyacrylamide gel.

Analysis of component 11 activity in proteins eluted from segments of the IEF gel indicated that a fraction with a pI of approximately 3.0 contained the active protein in component II. Protein from this gel slice was eluted and subjected to SDS-PAGE. Staining of the gel with Coomassie Blue revealed one prominent band of protein (molecular weight of about 28,000 Daltons) along with a smear of lower molecular weight proteins.

Component III. Component III of dicamba O-demethylase was retained on a Phenyl-Sepharose column in high concentrations of $(NH_4)_2SO_4$ and eluted at approximately 4% (w/v) $(NH_4)_2SO_4$. This light yellow fraction was tentatively identified as a reductase-containing fraction based on its ability to reduce oxidized cytochrome c and DCIP in the presence of NADH and because it could be replaced by cytochrome c reductase from porcine heart (Type 1, Sigma) in assays with components I and II. In this set of reactions, the use of 50 μg of partially purified component III produced a reaction rate of approximately 5 nmol min$^{-1}$ mg$^{-1}$ when mixed with an excess of components I and II. The highly purified cytochrome c reductase showed a specific activity of approximately 2.5 nmol min$^{-1}$ mg$^{-1}$ in the reaction, an activity well below that provided by component III when one considers the impurity of the crude component III used in these assays. In addition, component III exhibited reductase activity when incubated with cytochrome c or 2,6-dichlorophenol-indophenol (DCPIP) in the presence of NADH. Neither component I nor component II showed activity in either of these two reductase assays.

Additional purification of this fraction by chromatography on columns containing Q-Sepharose (Fast Flow), blue dye affinity matrix, Superose 12, and Mono Q packings resulted in low amounts of protein in the fractions with reductase activity. The component III protein was about 70% pure as judged by densitometric analysis of the active protein fraction after separation by SDS-PAGE and staining with Coomassie Blue.

To further exacerbate purification of component III, it was found that two different protein fractions from the Mono Q column step contained reductase activity when assayed with the ferredoxin and oxygenase components. Further purification of these two fractions by eletrophoresis on an IEF gel revealed that the reductase activities of the two fractions had distinctly different isoelectric points. This was demonstrated by excising lanes containing each of the two reductase fractions from the IEF gel and laying the slices on top of a pad of low melt agarose containing a DCIP reaction mixture. Reductase activity in both gel slices was identified by the NADH-dependent reduction of DCIP to its colorless, reduced form. The reductase in fraction 35 had an apparent pI of approximately 5.6 while the reductase in fraction 27 possessed an apparent pI of approximately 4.8.

Both reductase activities isolated from the IEF gel slices were unstable and present in low amounts. Indeed, only the reductase from fraction 35 from the Mono Q column fractionation retained sufficient protein concentration and activity to allow further purification and characterization. A slice from an IEF gel containing this reductase activity was eluted and separated from contaminating proteins by SDS-PAGE. The predominant protein in this gel was one with a mass of approximately 45,000 Daltons. Size exclusion chromatography had indicated an approximate molecular mass of 50,000 Daltons for component III in its native state.

Biochemical characteristics of dicamba O-demethylase. Dicamba O-demethylase activity was measured during incubations in vitro at temperatures ranging from 20° C. to 50° C. and at pH values from approximately 6 to 9. Activity peaked sharply at 30° C. and broadly at pH values between 6.5 and 7.5. Enzymatic activity was dependent on the type of pH buffer employed. At pH 7, for example, activity was approximately 40% lower in Tris-containing buffers than in phosphate-containing buffers.

Values for $K_m$ and $V_{max}$ for dicamba O-demethylase were estimated using SigmaPlot® to generate best fit curves from Michaelis-Menten and Lineweaver-Burk plots of data from duplicate experiments. The $K_m$ for dicamba was estimated to be approximately 9.9±3.9 μM and the $V_{max}$ for the reaction was estimated to be approximately 108 ±12 nmol/min/mg.

The three components were assayed for dicamba O-demethylase activity in various combinations. None of the components showed enzyme activity when assayed alone. Indeed, a significant amount of O-demethylase activity could be detected only when all three components were combined. A mixture of components I and II exhibited small amounts of enzyme activity, probably due to traces of component III contaminating the component I fractions.

Both NADH and NADPH supported enzyme activity, with NADH being markedly more effective than NADPH. $Mg^{2+}$ was necessary for enzyme activity. $Fe^{2+}$, flavin adenine dinucleotide (FAD), and flavin mononucleotide (FMN) produced little or no stimulation of enzymatic activity with the partially purified protein preparations in these experiments. The highest activity was obtained using a combination of NADH, $Fe^{2+}$, $Mg^{2+}$, and FAD.

DISCUSSION

Dicamba O-demethylase from *Pseudomonas maltophilia*, strain DI-6, is a three component oxygenase (Wang, X-Z (1996) Ph.D. thesis, University of Nebraska-Lincoln, Lincoln, Nebr.) responsible for the conversion of the herbicide, dicamba (2-methoxy-3,6-dichlorobenzoic acid), to 3,6-dichlorosalicylic acid (3,6-DCSA; 2-hydroxy-3,6-dichlorobenzoic acid). Purification schemes have been devised which have allowed the isolation of each of the three components to a homogeneous or near-homogeneous state.

Initial separation of the three components was achieved by chromatography on a Phenyl-Sepharose column. Enzymatic activities and other characteristics of the partially purified components allowed a tentative identification of the components as a reductase, a ferredoxin and an oxygenase—a composition similar to that found in a number of other previously studied heme-containing and nonheme-containing, multicomponent oxygenases (Batie, et al. (1992) pages 543-565, In F. Muller (ed.), *Chemistry and biochemistry of flavoenzymes*, vol. III, CRC Press, Boca Raton; Harayama, et al. (1992) *Annu. Rev. Microbiol.* 46:565-601; Mason and Cammack (1992) *Annu. Rev. Microbiol.* 46:277-305; Rosche et al. (1995) *Biochem. Biophys. Acta* 1252:177-179). Component III isolated from the Phenyl-Sepharose column catalyzed the NADH-dependent reduction of both cytochrome c and the dye, DCIP. In addition, its ability to support conversion of dicamba to 3,6-DCSA when combined with components I and II could be replaced in part by cytochrome c reductase. Component II could be replaced by the addition of ferredoxin from *Clostridium pasteurianum* to reactions containing components I and III. The absolute need for molecular oxygen to support the O-demethylation reaction indicated that the remaining component was an oxygenase.

Oxygenase$_{DIC}$. Component I of dicamba O-demethylase (designated as oxygenase$_{DIC}$) has been purified to homogeneity and subjected to N-terminal amino acid sequencing. The resulting sequence of twenty nine amino acid residues showed no significant homology to other protein sequences in the various data banks. However, the information obtained from this amino acid sequence permitted the design of degenerate oligonucleotide probes which have been successfully used to detect and clone the component I gene (see Example 2). Furthermore, a comparison of the amino acid sequence derived from the nucleotide sequence of this clone with that of the protein sequences in the data base showed strong homology to other oxygenases (see Example 2).

The apparent molecular mass of oxygenase$_{DIC}$, estimated from its migration in SDS-polyacrylamide gels, is approximately 40,000 Daltons. Purified preparations of the oxygenase exhibited only one major band on SDS-polyacrylamide gels stained with Coomassie Blue and Edman degradation of the protein contained in that band indicated the presence of only one N-terminal species. Estimates derived from the behavior of native oxygenase$_{DIC}$ on size exclusion columns suggests a molecular size of approximately 90,000 Daltons. All of these results suggest that the native oxygenase exists as a homodimer.

The oxygenase/hydroxylase component of a number of multicomponent systems is composed of an $(\alpha\beta)_n$-type subunit arrangement in which the larger $\alpha$ subunit is approximately 50,000 Daltons in size and the smaller $\beta$ subunit is approximately 20,000 Daltons in molecular mass (Harayama, et al. (1992) *Annu. Rev. Microbiol.* 46:565-601). In contrast, the oxygenase component of dicamba O-demethylase appears to possess a single subunit of approximately 40 kDa in molecular mass which may exist as a dimer in its native state. This $(\alpha)_n$-type subunit arrangement is similar to that found in other well characterized oxygenases such as 4-chlorophenylacetate 3,4-dioxygenase from *Pseudomonas* sp. strain CBS (Markus, et al. (1986) *J. Biol. Chem.* 261:12883-12888), phthalate dioxygenase from *Pseudomonas cepacia* (Batie, et al. (1987) *J. BioL Chem.* 262:1510-1518),4-sulphobenzoate 3,4-dioxygenase from *Comamonas testosteroni* (Locher, et al. (1991) *Biochem. J*,274:833-842), 2-oxo- 1,2-dihydroquinoline 8-monooxygenase from *Pseudomonas putida* 86 (Rosche et al. (1995) *Biochem. Biophys. Acta* 1252: 177-179), 4-carboxydiphenyl ether dioxygenase from *Pseudomonas pseudoalcaligenes* (Dehmel, et al. (1995) *Arch. Microbiol.* 163:35-41), and 3-chlorobenzoate 3,4-dioxygenase from *Pseudomonas putida*, (Nakatsu, et al. (1995) *Microbiology* (Reading) 141:485-495).

Ferredoxin$_{DIC}$. Component II (ferredoxin$_{DIC}$) of dicamba O-demethylase was purified by several steps of column chromatography and IEF. Final purification by SDS-PAGE produced one major band of protein ($M_r$~28,000) and a smear of slightly smaller proteins.

The N-terminal amino acid sequence of the protein with an apparent molecular weight of approximately 28,000 Daltons was determined. This amino acid sequence permitted the preparation of degenerate oligonucleotide probes, and these probes were used to isolate a genomic clone coding for this protein. Although the protein produced by this clone was a ferredoxin (ferrodoxin$_{28kDa}$), it was subsequently determined not to be active in the degradation of dicamba when combined with the other two components of dicamba O-demethylase (data not shown).

Other evidence supports the conclusion that ferrodoxin$_{28kDa}$ is not the ferredoxin component of dicamba O-demethylase. First, the molecular mass of this protein(28 kDa) protein is significantly higher than that of the other ferredoxins found in multicomponent oxygenases from bacteria (i.e., 8-13 kDa) (Batie, et al. (1992) pages 543-565, In F. Müller (ed.), *Chemistry and biochemistry of flavoenzymes*, vol. III, CRC Press, Boca Raton; Harayama, et al. (1992) *Annu. Rev. Microbiol.* 46:565-601).

Second, a comparison of the N-terminal sequence of 20 amino acid residues obtained from ferredoxin$_{28kDa}$ to other amino acid sequences in the various protein data banks using Genetics Computing Group (GCG) software package (University of Wisconsin, Madison, Wis.) revealed strong homology (80-85% identity compared to the most likely N-terminal sequence of ferredoxin$_{28kDa}$ to a number of dicluster bacterial ferredoxins (those from *Pseudomonas stutzeri, Pseudomonas putida, Rhodobacter capsulatus* and *Azotobacter Vinelandii*). The four dicluster ferredoxins which showed strong homology to ferredoxin$_{28kDa}$ have a [3Fe-4S] cluster followed by a [4Fe-4S] cluster at the N-terminus of the protein. This suggests that ferredoxin$_{28kDa}$ is distinctly different from the ferredoxin components with [2Fe-2S] clusters which are usually associated with non-heme multicomponent oxygenases (Harayama, et al. (1992) *Annu. Rev. Microbiol.* 46:565-601; Mason and Cammack (1992) *Annu. Rev. Microbiol.* 46:277-3 05; Rosche, et al. (1995) *Biochem. Biophys. Acta* 1252:177-179).

Reductase$_{DIC}$. Component III of dicamba O-demethylase (designated as reductased$_{DIC}$) has been the most recalcitrant of the three components to purify. This is due in part to its apparent instability and low abundance in lysates of strain DI-6. Nonetheless, sufficient protein has been purified to assign a tentative molecular mass of 45,000 Daltons. This is similar to the molecular mass of approximately 50,000 Daltons obtained from size exclusion chromatography and suggests that reductase$_{DIC}$ exists in its native form as a monomer. The purification of the reductase component has been further complicated by the fact that chromatography on a Mono Q column and IEF resolves purified reductase preparations into two activities with apparently distinct pI values. Both fractions from the Mono Q column functioned in combination with purified ferredoxin$_{DIC}$ and oxygenase$_{DIC}$ to produce dicamba O-demethylase activity. The presence in *Sphingomonas* sp. strain RW1 of two similar flavoproteins which function equally well as reductase components in the three component dibenzofuran 4,4a-dioxygenase has recently been reported by Bünz and Cook (Bünz and Cook (1993) *J. Bacteriol.* 175:6467-6475). Interestingly, both reductases were 44,000 Daltons in molecular mass, quite similar to that of the 45,000 Dalton reductase$_{DIC}$. Multiple components of leghemoglobin reductase have also been observed in lupin root nodules using isoelectric focusing techniques (Topunov, et al. (1982) *Biokhimiya* (English edition) 162:378-379). In this case, IEF revealed four separate components with NADH-dependent reductase activity. The resolution of the question of whether there is only one reductaseDIC which exists in two forms or two distinct reductases in strain DI-6 will rely on the development of improved procedures for isolating larger quantities of the proteins and/or on the cloning and sequencing of the gene(s) involved (see Examples 3 and 5).

Dicamba O-demethylase characteristics. In addition to the physical and biochemical properties of the individual components noted above, analyses of enzymatic activity have shown that the O-demethylase system has a strong affinity ($K_m$=~10 µM) for its substrate and a $V_{max}$ of approximately 100- 110 nmol/min/mg. As expected for a soil bacterium collected in a temperate climatic zone, the maximal enzymatic activity was observed at temperatures near 30° C. While the pH optima for the enzyme system was in the range from pH 6.5 to pH 7.5, the activity measured with a given preparation of enzyme was strongly affected by the type of pH buffering system employed. Activity in the presence of Tris buffers was at least 40% lower than with phosphate buffers at the same pH.

The reaction scheme for the reaction catalyzed by the three components of dicamba O-demethylase is presented in FIG. 1. Electrons from NADH are shuttled through a short electron chain consisting of the reductase and ferredoxin to the terminal oxygenase which catalyzes the oxidation of dicamba. The similarities between dicamba O-demethylase and several multicomponent dioxygenases suggest that dicamba O-demethylase may potentially possess cryptic dioxygenase activity. It is clear, however, that this enzyme is not in the class of dioxygenases which split $O_2$ and incorporate one atom of oxygen into the major substrate and the other into a small organic substrate such as a-ketoglutarate (Fukumori and Hausinger (1993) *J. BioL Chem.* 268:24311-24317). Indeed, combinations of highly purified reductase$_{DIC}$, ferredoxin$_{DIC}$, and oxygenase$_{DIC}$ require only $O_2$, NADH, $Mg^{2+}$, $Fe^{2+}$, and dicamba for activity.

Example 2

Identification And Sequencing Of A Clone Coding For The Oxygenase Of Dicamba O-Demethylase Of *Pseudomonas maltophilia* DI-6

As noted in Example 1, the first 29 amino acids of the N-terminal amino acid sequence of oxygenase$_{DIC}$ had been determined to be (residues in parentheses are best guesses):

Thr Phe Val Arg Asn Ala Trp Tyr Val Ala Ala Leu Pro Glu Glu Leu Ser Glu Lys Pro Leu Gly Arg Thr Ile Leu Asp (Asp or Thr) (Pro)

[SEQ ID NO:1].

This sequence permitted the design of degenerate oligonucleotide probes which were synthesized by Operon, Alameda, Calif. In particular, a mixture of 32 probes, each of which was 17 nucleotides in length, and contained all of the possible nucleotide sequences which could encode the amino acid sequence highlighted in bold above, was used. The oligonucleotide probes were 3'-end-labeled with digoxigenin (DIG) according to instructions provided by Boehringer Mannheim, Indianapolis, Ind.

The DIG-labeled probes were first hybridized to *P. maltophilia* DI-6 genomic DNA which had been digested with various combinations of restriction enzymes, resolved on a 1% agarose gel, and blotted to a nylon filter. Based on these results, a size-fractionated genomic library was constructed in the pBluescript II KS+ vector and transformed into *Escherichia coli* DH5αcompetent cells. The genomic library contained 1-2 kb Xho I/Hind III fragments. The DIG-labeled oligonucleotide probes were hybridized to an array of bacterial colonies streaked on nylon filters. Plasmid DNA was isolated from positive colonies and subcloned. Both strands of each subclone were sequenced by the DNA Sequencing Facility at the University of Nebraska-Lincoln. Hybridization and detection of DIG-labeled probes were performed according to protocols provided by Boehringer Mannheim.

A genomic DNA clone coding for the oxygenase$_{DIC}$ was identified. The nucleotide sequence and the deduced amino acid sequence of the entire oxygenase$_{DIC}$ are given in the Sequence Listing below as SEQ ID NO:2 and SEQ ID NO:3, respectively.

A comparison of the amino acid sequence derived from the nucleotide sequence of this clone with that of the protein sequences in the Swiss Protein Database showed homology to other oxygenases. Homology was determined using the FASTA program of the GCG software package. The strongest homology was with the oxygenase component of vanillate demethylase (from *Pseudomonas* sp., ATCC strain 19151) which showed 33.8% identity.

Example 3

Purification And Characterization Of Components Of Dicamba O-Demethylase Of *Pseudomonas maltophilia* DI-6

Bacterial cultures and preparation of cleared cell lysates. *Pseudomonas maltophilia*, strain DI-6, was inoculated into six two-liter Erlenmeyer flasks containing one liter of reduced chloride medium (Kreuger, J. P. 1989. Ph.D. thesis. Illinois Institute of Technology, Chicago) supplemented with glucose (2.0 mg/ml) and Casamino acids (2.0 mg/ml) as the carbon sources. Cultures were incubated on an orbital shaker (225 rpm at 30° C.). Cells were harvested at an $A_6$00 ranging from 1.5 to 2.0 using a JLA-10.500 rotor in a Beckman Avanti J-251 Centrifuge at 4,000×g for 20 minutes. Pelleted cells were stored at −80° C. The frozen cells were resuspended in 40 ml of 100 mM $MgCl_2$, pelleted again using the same conditions as above, and then resuspended in breaking buffer (100 mM 3-[N-morpholino]propanesulfonic acid (MOPS) (pH 7.2), 1 mM dithiothreitol, 5% glycerol) in a ratio of 2 ml breaking buffer per gram of cells wet weight. Lysozyme was added in a ratio of 80 µl per gram of cells along with a Protease Inhibitor Cocktail for bacterial extracts (Sigma, P 8465) in a ratio of 5 ml per 20 grams of cells wet weight. Finally, phenylmethylsulfonyl fluoride (0.1 M stock solution in 100% ethanol) was added in a ratio of 250 µl per 50 ml of breaking buffer. The cells were disrupted with a sonicator (Sonics and Materials Inc., Model VCX 600) in 9.0 second bursts, with 3.0 second resting periods, for 30 minutes at an amplitude of 50%. Lysed cells were centrifuged for 75 minutes at 56,000×g in a JA-25.50 rotor of a Beckman Avanti J-251 Centrifuge at 4° C. The supernatant (cleared cell lysate) was decanted and glycerol was added to a final concentration of 15% prior to storage at −80° C.

Initial purification of dicamba O-demethylase components. An aliquot of the cleared cell lysate containing approximately 2.7 grams of protein was applied to a Pharmacia XK 26/60 column containing 25 ml of DEAE-Sepharose Fast Flow equilibrated with 50 mM MOPS (pH7.2), 1 mM dithiothreitol, and 15% (v/v) glycerol (buffer A). The column was connected to a Bio-CAD Perfusion Chromatography Workstation (USDA NRICGP Grant # 9504266) and run at a flow rate of 5.0 ml/min. After the column was loaded, it was washed with buffer A until the absorbance reading at 280 nm decreased to below 0.1. All three components of dicamba O-demethylase were bound to the DEAE column under these conditions. The column was developed with a linear gradient of 0 to 500 mM NaCl in buffer A. This resulted in the elution of the ferredoxin at 400 mM NaCi and the co-elution of the reductase and oxygenase components at 250 mM NaCl.

Purification of the ferredoxin$_{DIC}$. Fractions containing the ferredoxin$_{DIC}$ eluted from the DEAE-Sepharose column were pooled and buffer exchanged into 50 mM MOPS (pH 7.2), 5% glycerol (v/v) and 200 mM NaCl (buffer B). They were then concentrated to approximately 2 ml using a Amicon Cell Concentrator with a YM10 membrane and a Centricon 10 concentrator. This sample was then applied to a pre-packed Pharmacia HiPrep 26/60 Sephacryl S-100 column equilibrated with buffer B and run at a flow rate of 0.5 ml/min on a Pharmacia FPLC apparatus. Fractions that showed activity were pooled and buffer exchanged into 50 mM MOPS (pH 7.2), 1 mM dithiothreitol and 5% glycerol (v/v) (buffer C). The fractions were concentrated to approximately 2ml and then loaded onto a Pharmacia Mono Q HR 5/5 column equilibrated in buffer C. The column was developed with a linear gradient of 0-2.0 M NaCl in buffer C. Fractions that contained ferredoxin activity were assayed for protein content and stored at −80° C.

Puirfication of the reductase$_{DIC}$. Fractions from the initial DEAE-Sepharose column containing the oxygenase/reductase components were pooled, and ammonium sulfate was added to a final concentration of 1.5 M. After incubating at 4° C. for 1.5 hours, the samples were centrifuged for 75 minutes at 56,000 x g at 4° C. in a JA-25.50 rotor of a Beckman Avanti J-251 centrifuge. The supernatant was retained and loaded at a flow rate of 5.0 ml/min onto a Pharmacia XK 26/20 column containing 25 ml of Phenyl-Sepharose 6 Fast Flow (high sub) that was equilibrated in buffer A containing 1.5 M $(NH_4)_2SO_4$. Fractions that contained the reductase component were pooled, buffer exchanged into buffer B, and concentrated to approximately 2 ml using the Amicon concentrator with an YM30 membrane and a Centricon 10 concentrator. The 2 ml sample was applied to a pre-packed Pharmacia HiPrep 26/60 Sephacryl S-100 column equilibrated in buffer B and run at 0.5 ml/min. Fractions containing reductase activity were pooled, buffer exchanged into buffer C, and concentrated down to approximately 2 ml. The 2 ml sample was loaded onto a pre-packed Pharmacia Mono Q HR 5/5 column that was equilibrated in buffer C. The column was developed with a linear gradient of 0-2.0 M NaCl in buffer C at a flow rate of 0.5 ml/min. Fractions that showed reductase activity were assayed for protein content and stored at −80° C.

Rapid enzyme assays. Activity for each of the three individual components was monitored in reactions using $^{14}$C-labeled dicamba in a reaction containing an excess of the remaining two components. For each reaction, a buffer solution composed of 24 mM potassium phosphate ($KP_i$) buffer (pH 7.0), 0.48 mM NADH, 0.48 mM $FeSO_4$ and 9.6 mM $MgCl_2$ was added to 200 µl of protein sample along with 30 µl of master mix (562.4 µl sterile water, 12.0 µl 50 mM dicamba and 25.6 µl $^{14}$C-dicamba stock solution [1.28µCi]) for a total volume of 311 µl and a $^{14}$C-dicamba specific activity of 4.12 µC$_i$/ml. After 60 min, each reaction was stopped by the addition of 50 µl 5% $H_2SO_4$ (v/v) and 500 µl ether. Reaction tubes were vortexed and centrifuged in a microfuge (Eppendorf, Model 5415C) at 14,000×g for 2 minutes. For a quick visual appraisal of enzymatic activity, each reaction tube was placed under a hand-held UV light (Fotodyne Inc., Model 3-6000) to detect fluorescence of the reaction product, DCSA. For more accurate, semi-quantitative measurements of enzymatic activities, reaction products were separated using thin layer chromatography as described in Example 1.

Protein concentration determinations. The fractions obtained at different stages of the purification protocol were assayed for protein concentration using the Bradford assay (standard protocol; Bio-Rad; see Example 1).

Example 4

Identification and Sequencing of a Clone Coding for Ferredoxin$_{DIC}$

The N-terminal sequence obtained from the purified ferredoxin protein (purification described in Example 3) was 29 amino acids in length (sequencing of proteins was performed by the Protein Core Facility at the University of Nebraska-Lincoln using a standard Edman degradation procedure; see Example 1). A comparison of this sequence to the Genbank database showed that it was 35% identical in a 26 amino acid overlap to a terpredoxin from *Pseudomonas* sp., a bacterial [2Fe-2S] ferredoxin in the adrenodoxin family. The sequence information was used to design three degenerate oligonucleotide primers (two forward and one reverse). The sequence of the two 17mer forward primers was based on the N-terminal amino acid sequence obtained from the purified ferredoxin protein. The sequence of the 17mer reverse primer was based on a conserved sequence of six amino acids near the C-terminal end of six previously sequenced bacterial adrenodoxin-type ferredoxins. The primers were used in a nested PCR reaction to amplify a 191 bp product from total *P. maltophilia* DNA. The product was cloned into the pGEM-T Easy vector (Promega, Madison, Wis.) and sequenced. DNA sequencing was performed by the DNA Sequencing Core Facility at the University of Nebraska-Lincoln using a standard dideoxy-mediated chain termination procedure. An analysis of the predicted amino acid sequence of this clone confirmed that it matched the N-terminal and internal amino acid sequence previously obtained from the purified ferredoxin protein. Furthermore, the derived amino acid sequence had 48% identity over its entire length with a [2Fe-2S] ferredoxin from *Rhodobacter capsulatus*. The cloned fragment was labeled with digoxigenin (DIG) (Roche Diagnostics) using a standard PCR protocol (DIG/Genius System User's Guide) and hybridized by a Southern blot to total *P. maltophilia* DNA that had been digested with a number of restriction enzymes. A map of the restriction sites surrounding the gene was constructed based on the sizes of the restriction fragments that hybridized to the probe. This initial experiment showed that the gene was contained on a Xho I/Pst I fragment that was approximately 1 kb in length. Subsequently, total *P. maltophilia* DNA was digested with Xho I and Pst I, and the restriction fragments were resolved on a gel. Fragments between 0.5 and 1.5 kb in length were excised from the gel, ligated into the vector pBluescript II KS+ (Stratagene, Inc.) and transformed into DH5α cells (Gibco BRL, Inc.). Bacterial colonies containing the size-fractionated library were screened with the DIG-labeled probe and a 900 bp Xho I/Pst I fragment was identified. Sequence analysis showed that this clone contained a full-length 318 bp ferredoxin gene [SEQ ID NO:4] that encoded an 11.4 kDa protein composed of 105 amino acid residues [SEQ ID NO:5]. The amino acid sequence predicted by the cloned gene matched the N-terminal and internal amino acid sequence previously obtained from the purified ferredoxin protein. Furthermore, the predicted amino acid sequence was homologous over its entire length to five other members of the adrenodoxin family of [2Fe-2S] bacterial ferredoxins, ranging from 42% identity with a ferredoxin from *Rhodobacter capsulatus* to 35% identity with a ferredoxin from *Pseudomonas* (see FIG. 2). The other three ferredoxins were from *Caulobacter crescentus, Rhodococcus erythropolis*, and *Pseudomonas putida*. Proteins in this family bind a single 2Fe-2S iron-sulfur cluster and have three conserved motifs. Motif 1 includes three conserved cysteines which are 2Fe-2S ligands. Motif 2 contains a cluster of negatively charged residues. Motif 3 includes the fourth conserved cysteine of the 2Fe-2S cluster.

Example 5

Identification and Sequencing Of Clones Coding Reductase$_{DIC}$

Two reductase genes were cloned by the same approach that was used in Example 4 to clone the ferredoxin gene. The N-terminal sequence obtained from the purified reductase protein (purification described in Example 3) was 25 amino acids in length. A comparison of this sequence to the Genbank database showed that it was 90% identical in a 20 amino acid overlap to a cytochrome P450-type reductase component of dioxin dioxygenase, a three component enzyme previously isolated from *Sphingomonas* sp. RW1. An internal sequence of 10 amino acid residues was also obtained from tryptic digests of the purified protein. The internal sequence had 87.5% identity with residues 62 through 69 of the same cytochrome P450-type reductase from *Sphingomonas* sp. RW1. This sequence information was used to design three degenerate oligonucleotide primers (two forward and one reverse). The sequence of the two 17mer forward primers was based on the N-terminal amino acid sequence and the sequence of the 17mer reverse primer was based on the internal amino acid sequence. The primers were used in a nested PCR reaction to amplify a 180 bp product from total *P. maltophilia* DNA. The product was cloned into the pGEM-T Easy vector and sequenced. An analysis of the predicted amino acid sequence of this clone confirmed that it encoded a protein that matched the N-terminal and internal amino acid sequence obtained from the purified reductase protein. Furthermore, the predicted sequence had 80% identity over its entire length with the cytochrome P-450 type reductase component s of the dioxin dioxygenase from *Sphingomonas* sp. RW1.

The cloned fragment was labeled with DIG and hybridized by a Southern blot to total *P. maltophilia* DNA that had been digested with a number of restriction enzymes. The Southern blot showed that the DIG-labeled probe recognized two distinct loci in the various restriction digests of *P. maltophilia* total DNA. This observation suggested that there are two reductase genes located at different positions in the genome of *P. maltophilia* . It was possible that the two genes are identical duplications that encode identical reductase proteins. Alternatively, one of the genes could encode a truncated protein with no activity or a full-length protein with low activity in our dicamba O-demethylase assay. Because it was necessary to clone the gene that encodes a protein with optimal activity, the DIG-labeled probe was used to retrieve both reductase genes.

When total *P. maltophilia* DNA was digested with Kpn I and EcoR I, the DIG-labeled probe hybridized to one restriction fragment that was approximately 4.0 kb in length and to another larger fragment with a size of approximately 20 kb. A map of a number of restriction sites surrounding the gene located on the 4.0 kb Kpn I/EcoR I fragment was constructed based on the sizes of different restriction fragments that hybridized to the probe. The restriction map indicated that the entire gene should be located on this 4.0 kb fragment. Subsequently, total *P. maltophilia* DNA was digested with Kpn I and EcoR I, and the restriction fragments were resolved on a gel. Fragments between 3.0 and 5.0 kb in length were excised from the gel, ligated into the vector pBluescript II KS+, and transformed into DH5α cells. Bacterial colonies containing the size-fractionated library were screened with the DIG-labeled probe and a 4.3 kb Kpn I/EcoR I fragment was identified. Sequence analysis showed that this clone contained a full-length 1224 bp reductase gene [SEQ ID NO:6] and encoded a 43.7 kDa protein consisting of 408 amino acids [SEQ ID NO:7]. The amino acid sequence predicted by the cloned gene matched the N-terminal and internal amino acid sequence previously obtained from the purified reductase protein. Furthermore, the predicted amino acid sequence was homologous over its entire length to at least four other FAD-dependent pyridine nucleotide reductases, ranging from 69% identity with a cytochrome P450-type reductase component of dioxin dioxygenase from *Sphingomonas* sp. RW 1 to 36% identity with the terpredoxin reductase from a *Pseudomonas* species (see FIG. 3). The two other FAD-dependent pyridine nucleotide reductases were from *R. erythropolis* and *P. putida*. Proteins in this family of FAD-dependent pyridine nucleotide reductases have five conserved motifs. Motifs 1 and 3 contain three conserved glycine residues and correspond to the ADP binding site for FAD and NAD(P) respectively. Motif 5 corresponds to the site binding the FAD flavin moiety.

To clone the second gene, total *P. maltophilia* DNA was digested with Kpn I and EcoR I and the resulting restriction fragments were resolved on an agarose gel. Fragments with a size of approximately 20 kb were excised from the gel, digested with a number of restriction enzymes, and then hybridized by Southern blot to the DIG-labeled probe. A map of the restriction sites surrounding the second gene was constructed based on the sizes of the restriction fragments that hybridized to the probe. These experiments showed that the full-length second reductase gene was contained on an Apa I fragment that was approximately 3.0 kb in length. Subsequently, total *P. maltophilia* DNA was digested with Apa I and the restriction fragments were resolved on a gel. Fragments between 2.0 and 4.0 kb in length were excised from the gel, ligated into the vector pBluescript II KS+, and transformed into DH5α cells. Bacterial colonies containing the size-fractionated library were screened with the DIG-labeled probe and a 3.0 kb Apa I fragment was identified. Sequence analysis showed that the 3.0 kb clone contained an open reading frame of 1227 bp [SEQ ID NO:8] and encoded a 43.9 kDa protein consisting of 409 amino acids [SEQ ID NO:9]. The amino acid sequence encoded by the second reductase gene is almost identical (98.8% identity) to the sequence of the first gene.

Example 6

Transformation Of Plants

In order to place each of the three genes that encode the components of dicamba 0-demethylase individually into cassettes suitable for expression in plants, the following steps were taken. Oligonucleotide primers were designed to generate a Nco I site at the 5' end and an Xba I site at the 3' end of each of the three genes by PCR amplification. The authenticity of the resulting PCR products was confirmed by sequencing, and each gene was then cloned individually into the pRTL2 vector (provided by Dr. Tom Clemente of the Plant Transformation Core Research Facility, University of Nebraska, Lincoln, Nebr.). This vector contains a 144 bp translation enhancer sequence from tobacco etch virus (TEV) (Carrington and Freed, *J. Virology,* 64:1590-1597(1990)) at the 5' end of the polylinker. The oxygenase, reductase, and ferredoxin genes, each with a 5' translation enhancer, were then cloned individually as Xho I/Xba I fragments into the plant expression vector pKLP36 (obtained from Indu Maiti, University of Kentucky, Lexington, Ky.) (Maiti and Shepard, Biochem. Biophys. Res. Commun., 244:440-444 (1998)). This binary vector contains the peanut chlorotic virus full-length promoter (PCISV FLt36) with a duplicated enhancer domain for constitutive expression in plants and the pea rbcS 3' sequence for efficient transcript termination (Maiti and Shepherd, *Biochem. Biophys. Res. Commun.,* 244:440-444 (1998)). Constructs with all three genes on one binary vector can be produced using combinations of the three genes in a number of different orders and orientations.

The following methods were employed to move the oxygenase, ferredoxin, and reductase constructs individually into *Agrobacterium tumefaciens* and to transform each construct into *Arabidopsis* and tobacco. The three constructs were moved into the *A. tumefaciens* strain C58C1 by a modified triparental mating procedure routinely used by the Plant Transformation Core Research Facility. This involved incubating *Escherichia coli* cells carrying each construct with a mixture of *A. tumefaciens* cells and *E. coli* cells carrying the helper plasmid pRK2013 (for plasmid mobilization). *A. tumefaciens* cells containing each of the constructs were then used to transform tobacco and *Arabidopsis* with the assistance of the Plant Transformation Core Research Facility. For tobacco, leaf explants were incubated with a suspension of *A. tumefaciens* cells containing each of the constructs, and shoots were regenerated on solid medium containing kanamycin (Horsch et al., *Science,* 227:1229-1231 (1985)). Ten shoots were selected from each of the three transformation experiments, placed on rooting medium for a few weeks, and then moved to pots in the greenhouse. For *Arabidopsis,* a pot of plants with flowers was incubated with a suspension of *A. tumefaciens* cells containing each of the constructs, and the plants were then allowed to set seed (Bechtold et al., *C. R. Acad. Sci. Paris, Sciences de la vie/Life sciences,* 316:1194-1199 (1993); Clough and Bent, Plant J, 16(6):735-743 (1998)). The seed was collected and germinated on medium with kanamycin. After the seedlings had developed an adequate root system, several plants were selected from each transformation experiment and moved to pots in a growth chamber.

For evaluation of the expression of each gene in the transformed plants, Western blots of leaf lysates from several transformed plants were prepared and probed with polyclonal antibodies that detect the three components of dicamba O-demethylase. To determine enzyme activities for each enzyme in plant extracts, the approach was to combine leaf lysates from transformed plants expressing the oxygenase, ferredoxin or reductase proteins with excess amounts of the other O-demethylase components purified from *P. maltophilia* strain DI-6. These mixtures were tested for dicamba O-demethylase activity with both the standard $^{14}$C-labeled dicamba assay (see Examples 1 and 3) and an HPLC assay employing nonradioactive dicamba as substrate (dicamba and 3,6-DCSA elute at different points from the HPLC and can be quantitated).

To test expression of gene products in the chloroplast compartment, constructs were made with a transit peptide sequence at the 5' end of the oxygenase, ferredoxin, and reductase genes. Such an approach was successful for introducing tolerance to the sulfonylurea herbicides into tobacco plants (O'Keefe et al., *Plant Physiol.,* 105:473-478 (1994)).

To test the possibility that the codon usage of the bacterial ferredoxin gene was not fully optimal for efficient translation in a plant cell, a synthetic ferredoxin gene encoding the same amino acid sequence as the *P. maltophilia* strain DI-6 ferredoxin, but with optimized codon bias for dicot plants was synthesized by Entelechon, GmbH (Regensberg, Germany). It has been well documented that changes in codon usage are essential for optimal expression of the bacterial B.t. toxin genes in plant cells (see, e.g., Diehn et al., *Genetic Engineering,* 18:83-99 (1996)).

We claim:

1. A recombinant DNA molecule, consisting essentially of a DNA sequence encoding a dicamba-degrading oxygenase, wherein the DNA sequence encodes an amino acid sequence that differs from SEQ ID NO:3 by one substitution.

2. A recombinant DNA molecule, consisting essentially of a DNA sequence encoding a dicamba-degrading oxygenase, wherein the DNA sequence encodes an amino acid sequence that differs from SEQ ID NO:3 by one addition.

3. A plant transformation vector, comprising a DNA sequence encoding a dicamba-degrading oxygenase, wherein the DNA sequence encodes an amino acid sequence that differs from SEQ ID NO:3 by one substitution.

4. A plant transformation vector, comprising a DNA sequence encoding a dicamba-degrading oxygenase, wherein the DNA sequence encodes an amino acid sequence that differs from SEQ ID NO:3 by one addition.

5. A plant transformation vector, comprising a DNA sequence encoding a dicamba-degrading oxygenase, wherein the DNA sequence encodes an amino acid sequence that differs from SEQ ID NO:3 by one substitution and by one addition.

6. A plant transformation vector, comprising a DNA sequence encoding a dicamba-degrading oxygenase, wherein the DNA sequence encodes an amino acid sequence comprising SEQ ID NO:3.

7. A plant transformation vector, comprising a DNA sequence encoding a dicamba-degrading oxygenase, wherein the DNA sequence comprises SEQ ID NO:2.

8. A transgenic plant cell that has been transformed with the plant transformation vector of claim 3.

9. A transgenic plant cell that has been transformed with the plant transformation vector of claim 4.

10. A transgenic plant cell that has been transformed with the plant transformation vector of claim 5.

11. A transgenic plant cell that has been transformed with the plant transformation vector of claim 6.

12. A transgenic plant or part of said transgenic plant comprising one or more cells transformed with the plant transformation vector of claim 3.

13. A transgenic plant or part of said transgenic plant comprising one or more cells transformed with the plant transformation vector of claim 4.

14. A transgenic plant or part of said transgenic plant comprising one or more cells transformed with the plant transformation vector of claim 5.

15. A transgenic plant or part of said transgenic plant comprising one or more cells transformed with the plant transformation vector of claim 6.

16. A transgenic seed from a transgenic plant according to claim 12.

17. A transgenic seed from a transgenic plant according to claim 13.

18. A transgenic seed from a transgenic plant according to claim 14.

19. A transgenic seed from a transgenic plant according to claim 15.

* * * * *

SEQUENCE LISTING

```
<160> NUMBER OF SEQ ID NOS: 18

<210> SEQ ID NO 1
<211> LENGTH: 29
<212> TYPE: PRT
<213> ORGANISM: Pseudomonas maltophilia DI-6
<220> FEATURE:
<221> NAME/KEY: unsure
<222> LOCATION: (28)..(28)
<223> OTHER INFORMATION: Best guess for Xaa = Asp or Thr
<220> FEATURE:
<221> NAME/KEY: unsure
<222> LOCATION: (29)..(29)
<223> OTHER INFORMATION: Best guess for Xaa = Pro

<400> SEQUENCE: 1

Thr Phe Val Arg Asn Ala Trp Tyr Val Ala Ala Leu Pro Glu Glu Leu
1               5                   10                  15

Ser Glu Lys Pro Leu Gly Arg Thr Ile Leu Asp Xaa Xaa
            20                  25

<210> SEQ ID NO 2
<211> LENGTH: 1020
```

<212> TYPE: DNA
<213> ORGANISM: Pseudomonas maltophilia DI-6
<220> FEATURE:
<221> NAME/KEY: CDS
<222> LOCATION: (1)..(1020)

<400> SEQUENCE: 2

```
atg acc ttc gtc cgc aat gcc tgg tat gtg gcg gcg ctg ccc gag gaa      48
Met Thr Phe Val Arg Asn Ala Trp Tyr Val Ala Ala Leu Pro Glu Glu
1               5                   10                  15 ctg tcc gaa aag ccg ctc ggc cgg acg att ctc gac aca ccg ctc gcg      96
Leu Ser Glu Lys Pro Leu Gly Arg Thr Ile Leu Asp Thr Pro Leu Ala
            20                  25                  30 ctc tac cgc cag ccc gac ggt gtg gtc gcg gcg ctc ctc gac atc tgt     144
Leu Tyr Arg Gln Pro Asp Gly Val Val Ala Ala Leu Leu Asp Ile Cys
        35                  40                  45 ccg cac cgc ttc gcg ccg ctg agc gac ggc atc ctc gtc aac ggc cat     192
Pro His Arg Phe Ala Pro Leu Ser Asp Gly Ile Leu Val Asn Gly His
50                  55                  60 ctc caa tgc ccc tat cac ggg ctg gaa ttc gat ggc ggc ggg cag tgc     240
Leu Gln Cys Pro Tyr His Gly Leu Glu Phe Asp Gly Gly Gly Gln Cys
65                  70                  75                  80 gtc cat aac ccg cac ggc aat ggc gcc cgc ccg gct tcg ctc aac gtc     288
Val His Asn Pro His Gly Asn Gly Ala Arg Pro Ala Ser Leu Asn Val
                85                  90                  95 cgc tcc ttc ccg gtg gtg gag cgc gac gcg ctg atc tgg atc tgg ccc     336
Arg Ser Phe Pro Val Val Glu Arg Asp Ala Leu Ile Trp Ile Trp Pro
            100                 105                 110 ggc gat ccg gcg ctg gcc gat cct ggg gcg atc ccc gac ttc ggc tgc     384
Gly Asp Pro Ala Leu Ala Asp Pro Gly Ala Ile Pro Asp Phe Gly Cys
        115                 120                 125 cgc gtc gat ccc gcc tat cgg acc gtc ggc ggc tat ggg cat gtc gac     432
Arg Val Asp Pro Ala Tyr Arg Thr Val Gly Gly Tyr Gly His Val Asp
130                 135                 140 tgc aac tac aag ctg ctg gtc gac aac ctg atg gac ctc ggc cac gcc     480
Cys Asn Tyr Lys Leu Leu Val Asp Asn Leu Met Asp Leu Gly His Ala
145                 150                 155                 160 caa tat gtc cat cgc gcc aac gcc cag acc gac gcc ttc gac cgg ctg     528
Gln Tyr Val His Arg Ala Asn Ala Gln Thr Asp Ala Phe Asp Arg Leu
                165                 170                 175 gag cgc gag gtg atc gtc ggc gac ggt gag ata cag gcg ctg atg aag     576
Glu Arg Glu Val Ile Val Gly Asp Gly Glu Ile Gln Ala Leu Met Lys
            180                 185                 190 att ccc ggc ggc acg ccg agc gtg ctg atg gcc aag ttc ctg cgc ggc     624
Ile Pro Gly Gly Thr Pro Ser Val Leu Met Ala Lys Phe Leu Arg Gly
        195                 200                 205 gcc aat acc ccc gtc gac gct tgg aac gac atc cgc tgg aac aag gtg     672
Ala Asn Thr Pro Val Asp Ala Trp Asn Asp Ile Arg Trp Asn Lys Val
210                 215                 220 agc gcg atg ctc aac ttc atc gcg gtg gcg ccg gaa ggc acc ccg aag     720
Ser Ala Met Leu Asn Phe Ile Ala Val Ala Pro Glu Gly Thr Pro Lys
225                 230                 235                 240 gag cag agc atc cac tcg cgc ggt acc cat atc ctg acc ccc gag acg     768
Glu Gln Ser Ile His Ser Arg Gly Thr His Ile Leu Thr Pro Glu Thr
                245                 250                 255 gag gcg agc tgc cat tat ttc ttc ggc tcc tcg cgc aat ttc ggc atc     816
Glu Ala Ser Cys His Tyr Phe Phe Gly Ser Ser Arg Asn Phe Gly Ile
            260                 265                 270 gac gat ccg gag atg gac ggc gtg ctg cgc agc tgg cag gct cag gcg     864
Asp Asp Pro Glu Met Asp Gly Val Leu Arg Ser Trp Gln Ala Gln Ala
        275                 280                 285
```

```
ctg gtc aag gag gac aag gtc gtc gtc gag gcg atc gag cgc cgc cgc     912
Leu Val Lys Glu Asp Lys Val Val Val Glu Ala Ile Glu Arg Arg Arg
    290                 295                 300 gcc tat gtc gag gcg aat ggc atc cgc ccg gcg atg ctg tcg tgc gac     960
Ala Tyr Val Glu Ala Asn Gly Ile Arg Pro Ala Met Leu Ser Cys Asp
305                 310                 315                 320 gaa gcc gca gtc cgt gtc agc cgc gag atc gag aag ctt gag cag ctc    1008
Glu Ala Ala Val Arg Val Ser Arg Glu Ile Glu Lys Leu Glu Gln Leu
                325                 330                 335 gaa gcc gcc tga                                                    1020
Glu Ala Ala <210> SEQ ID NO 3
<211> LENGTH: 339
<212> TYPE: PRT
<213> ORGANISM: Pseudomonas maltophilia DI-6

<400> SEQUENCE: 3

Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
            20                  25                  30

Leu Tyr Arg Gln Pro Asp Gly Val Val Ala Ala Leu Leu Asp Ile Cys
        35                  40                  45

Pro His Arg Phe Ala Pro Leu Ser Asp Gly Ile Leu Val Asn Gly His
    50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
                85                  90                  95

Arg Ser Phe Pro Val Val Glu Arg Asp Ala Leu Ile Trp Ile Trp Pro
            100                 105                 110

Gly Asp Pro Ala Leu Ala Asp Pro Gly Ala Ile Pro Asp Phe Gly Cys
        115                 120                 125

Arg Val Asp Pro Ala Tyr Arg Thr Val Gly Gly Tyr Gly His Val Asp
    130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
        195                 200                 205

Ala Asn Thr Pro Val Asp Ala Trp Asn Asp Ile Arg Trp Asn Lys Val
    210                 215                 220

Ser Ala Met Leu Asn Phe Ile Ala Val Ala Pro Glu Gly Thr Pro Lys
225                 230                 235                 240

Glu Gln Ser Ile His Ser Arg Gly Thr His Ile Leu Thr Pro Glu Thr
                245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
        275                 280                 285

Leu Val Lys Glu Asp Lys Val Val Val Glu Ala Ile Glu Arg Arg Arg
```

```
                  290                  295                 300
Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
                325                 330                 335

Glu Ala Ala

<210> SEQ ID NO 4
<211> LENGTH: 318
<212> TYPE: DNA
<213> ORGANISM: Pseudomonas maltophilia DI-6
<220> FEATURE:
<221> NAME/KEY: CDS
<222> LOCATION: (1)..(318)

<400> SEQUENCE: 4 atg ccg cag att acc gtc gtc aac cag tcg ggt gaa gaa tcc agc gtc      48
Met Pro Gln Ile Thr Val Val Asn Gln Ser Gly Glu Glu Ser Ser Val
1               5                   10                  15 gag gcg agt gaa ggc cgc acc ctg atg gaa gtc atc cgc gac agc ggt      96
Glu Ala Ser Glu Gly Arg Thr Leu Met Glu Val Ile Arg Asp Ser Gly
                20                  25                  30 ttt gac gaa ctc ctg gcg ctt tgc ggc ggc tgc tgc tcg tgc gcg acc     144
Phe Asp Glu Leu Leu Ala Leu Cys Gly Gly Cys Cys Ser Cys Ala Thr
            35                  40                  45 tgc cac gtc cac atc gac ccg gcc ttc atg gac aag ctg ccg gag atg     192
Cys His Val His Ile Asp Pro Ala Phe Met Asp Lys Leu Pro Glu Met
        50                  55                  60 agc gaa gac gag aac gac ctg ctc gac agc tcg gac cac cgc aac gag     240
Ser Glu Asp Glu Asn Asp Leu Leu Asp Ser Ser Asp His Arg Asn Glu
65                  70                  75                  80 tac tcg cgt ctc tcg tgc cag att ccg gtc acc ggc gcc ctc gaa ggc     288
Tyr Ser Arg Leu Ser Cys Gln Ile Pro Val Thr Gly Ala Leu Glu Gly
                85                  90                  95 atc aag gtg acg atc gcg cag gaa gac tga                             318
Ile Lys Val Thr Ile Ala Gln Glu Asp
                100                 105

<210> SEQ ID NO 5
<211> LENGTH: 105
<212> TYPE: PRT
<213> ORGANISM: Pseudomonas maltophilia DI-6

<400> SEQUENCE: 5

Met Pro Gln Ile Thr Val Val Asn Gln Ser Gly Glu Glu Ser Ser Val
1               5                   10                  15

Glu Ala Ser Glu Gly Arg Thr Leu Met Glu Val Ile Arg Asp Ser Gly
                20                  25                  30

Phe Asp Glu Leu Leu Ala Leu Cys Gly Gly Cys Cys Ser Cys Ala Thr
            35                  40                  45

Cys His Val His Ile Asp Pro Ala Phe Met Asp Lys Leu Pro Glu Met
        50                  55                  60

Ser Glu Asp Glu Asn Asp Leu Leu Asp Ser Ser Asp His Arg Asn Glu
65                  70                  75                  80

Tyr Ser Arg Leu Ser Cys Gln Ile Pro Val Thr Gly Ala Leu Glu Gly
                85                  90                  95

Ile Lys Val Thr Ile Ala Gln Glu Asp
                100                 105
```

<210> SEQ ID NO 6
<211> LENGTH: 1227
<212> TYPE: DNA
<213> ORGANISM: Pseudomonas maltophilia DI-6
<220> FEATURE:
<221> NAME/KEY: CDS
<222> LOCATION: (1)..(1227)

<400> SEQUENCE: 6

| | | | | | | | | | | | | | | | | |
|---|---|---|---|---|---|---|---|---|---|---|---|---|---|---|---|---|
| atg | agc | aag | gca | gac | gtc | gta | atc | gtg | gga | gcc | ggg | cat | ggc | ggc | gca | 48 |
| Met | Ser | Lys | Ala | Asp | Val | Val | Ile | Val | Gly | Ala | Gly | His | Gly | Gly | Ala | |
| 1 | | | | 5 | | | | | 10 | | | | | 15 | | |
| cag | tgc | gcg | atc | gcc | ctt | cgc | cag | aac | ggc | ttc | gaa | gga | acc | atc | acc | 96 |
| Gln | Cys | Ala | Ile | Ala | Leu | Arg | Gln | Asn | Gly | Phe | Glu | Gly | Thr | Ile | Thr | |
| | | | 20 | | | | | 25 | | | | | 30 | | | |
| gtc | atc | ggt | cgt | gag | ccg | gaa | tat | ccc | tat | gag | cgt | ccg | ccg | ctc | tcg | 144 |
| Val | Ile | Gly | Arg | Glu | Pro | Glu | Tyr | Pro | Tyr | Glu | Arg | Pro | Pro | Leu | Ser | |
| | | 35 | | | | | 40 | | | | | 45 | | | | |
| aag | gaa | tat | ttc | gcg | cgc | gag | aag | acc | ttc | gac | cgc | ctc | tac | atc | cgt | 192 |
| Lys | Glu | Tyr | Phe | Ala | Arg | Glu | Lys | Thr | Phe | Asp | Arg | Leu | Tyr | Ile | Arg | |
| 50 | | | | | 55 | | | | | 60 | | | | | | |
| ccg | ccg | acg | ttc | tgg | gcc | gag | aag | aac | atc | gag | ttc | aag | ctt | ggc | acc | 240 |
| Pro | Pro | Thr | Phe | Trp | Ala | Glu | Lys | Asn | Ile | Glu | Phe | Lys | Leu | Gly | Thr | |
| 65 | | | | | 70 | | | | | 75 | | | | | 80 | |
| gaa | gtc | acc | aag | gtc | gat | ccc | aag | gcg | cac | gaa | ctg | acg | ctc | tcc | aac | 288 |
| Glu | Val | Thr | Lys | Val | Asp | Pro | Lys | Ala | His | Glu | Leu | Thr | Leu | Ser | Asn | |
| | | | | 85 | | | | | 90 | | | | | 95 | | |
| ggc | gag | agc | tac | ggt | tat | ggc | aag | ctc | gtc | tgg | gcc | acc | ggc | ggc | gat | 336 |
| Gly | Glu | Ser | Tyr | Gly | Tyr | Gly | Lys | Leu | Val | Trp | Ala | Thr | Gly | Gly | Asp | |
| | | | 100 | | | | | 105 | | | | | 110 | | | |
| ccg | cgt | cgc | ctt | tct | tgc | cag | ggg | gcc | gac | ctc | acc | ggc | atc | cac | gcc | 384 |
| Pro | Arg | Arg | Leu | Ser | Cys | Gln | Gly | Ala | Asp | Leu | Thr | Gly | Ile | His | Ala | |
| | | 115 | | | | | 120 | | | | | 125 | | | | |
| gtg | cgc | acc | cgc | gag | gac | tgc | gac | acg | ctg | atg | gcc | gaa | gtc | gat | gcg | 432 |
| Val | Arg | Thr | Arg | Glu | Asp | Cys | Asp | Thr | Leu | Met | Ala | Glu | Val | Asp | Ala | |
| | 130 | | | | | 135 | | | | | 140 | | | | | |
| ggc | acg | aag | aac | atc | gtc | gtc | atc | ggc | ggc | ggc | tac | atc | ggt | ctg | gaa | 480 |
| Gly | Thr | Lys | Asn | Ile | Val | Val | Ile | Gly | Gly | Gly | Tyr | Ile | Gly | Leu | Glu | |
| 145 | | | | | 150 | | | | | 155 | | | | | 160 | |
| gcc | gct | gcg | gtg | ctg | tcc | aag | atg | ggc | ctc | aag | gtc | acc | ctg | ctc | gaa | 528 |
| Ala | Ala | Ala | Val | Leu | Ser | Lys | Met | Gly | Leu | Lys | Val | Thr | Leu | Leu | Glu | |
| | | | | 165 | | | | | 170 | | | | | 175 | | |
| gcg | ctt | ccg | cgc | gtg | ctg | gcg | cgc | gtt | gcg | ggt | gaa | gac | ctc | tcg | acc | 576 |
| Ala | Leu | Pro | Arg | Val | Leu | Ala | Arg | Val | Ala | Gly | Glu | Asp | Leu | Ser | Thr | |
| | | | 180 | | | | | 185 | | | | | 190 | | | |
| ttc | tac | cag | aag | gaa | cat | gtc | gat | cac | ggc | gtc | gac | ctg | cgc | acc | gaa | 624 |
| Phe | Tyr | Gln | Lys | Glu | His | Val | Asp | His | Gly | Val | Asp | Leu | Arg | Thr | Glu | |
| | | 195 | | | | | 200 | | | | | 205 | | | | |
| gtc | atg | gtc | gac | agc | ctc | gtc | ggc | gaa | aac | ggc | aag | gtc | acc | ggc | gtg | 672 |
| Val | Met | Val | Asp | Ser | Leu | Val | Gly | Glu | Asn | Gly | Lys | Val | Thr | Gly | Val | |
| | 210 | | | | | 215 | | | | | 220 | | | | | |
| cag | ctt | gcc | ggc | ggc | gaa | gtg | atc | ccg | gcc | gaa | ggc | gtc | atc | gtc | ggc | 720 |
| Gln | Leu | Ala | Gly | Gly | Glu | Val | Ile | Pro | Ala | Glu | Gly | Val | Ile | Val | Gly | |
| 225 | | | | | 230 | | | | | 235 | | | | | 240 | |
| atc | ggc | atc | gtg | cct | gcc | gtc | ggt | ccg | ctg | atc | gcg | gcc | ggc | gcg | gcc | 768 |
| Ile | Gly | Ile | Val | Pro | Ala | Val | Gly | Pro | Leu | Ile | Ala | Ala | Gly | Ala | Ala | |
| | | | | 245 | | | | | 250 | | | | | 255 | | |
| ggt | gcc | aac | ggc | gtc | gac | gtg | gac | gag | tac | tgc | cgc | acc | tcg | ctg | ccc | 816 |
| Gly | Ala | Asn | Gly | Val | Asp | Val | Asp | Glu | Tyr | Cys | Arg | Thr | Ser | Leu | Pro | |
| | | | 260 | | | | | 265 | | | | | 270 | | | |
| gac | atc | tat | gcg | atc | ggc | gac | tgt | gcg | gct | ttc | gcc | tgc | gac | tac | gcc | 864 |

```
Asp Ile Tyr Ala Ile Gly Asp Cys Ala Ala Phe Ala Cys Asp Tyr Ala
            275                 280                 285 ggc ggc aac gtg atg cgc gtg gaa tcg gtc cag aac gcc aac gac atg      912
Gly Gly Asn Val Met Arg Val Glu Ser Val Gln Asn Ala Asn Asp Met
        290                 295                 300 ggc acc tgc gtg gcc aag gcg atc tgc ggc gac gag aag ccc tac aag      960
Gly Thr Cys Val Ala Lys Ala Ile Cys Gly Asp Glu Lys Pro Tyr Lys
305                 310                 315                 320 gcg ttc ccg tgg ttc tgg tcc aac cag tac gac ctc aag ctg cag acc     1008
Ala Phe Pro Trp Phe Trp Ser Asn Gln Tyr Asp Leu Lys Leu Gln Thr
                325                 330                 335 gcc ggc atc aac ctg ggc ttc gac aag acc gtg atc cgc ggc aat ccg     1056
Ala Gly Ile Asn Leu Gly Phe Asp Lys Thr Val Ile Arg Gly Asn Pro
            340                 345                 350 gag gag cgc agc ttc tcg gtc gtc tat ctc aag gac ggc cgc gtg gtc     1104
Glu Glu Arg Ser Phe Ser Val Val Tyr Leu Lys Asp Gly Arg Val Val
        355                 360                 365 gcg ctg gac tgc gtg aac atg gtc aag gat tac gtg cag ggc cgc aag     1152
Ala Leu Asp Cys Val Asn Met Val Lys Asp Tyr Val Gln Gly Arg Lys
370                 375                 380 ctg gtc gaa gcc ggg gcc acc ccc gac ctc gaa gcg ctg gcc gat gcc     1200
Leu Val Glu Ala Gly Ala Thr Pro Asp Leu Glu Ala Leu Ala Asp Ala
385                 390                 395                 400 ggc aag ccg ctc aag gaa ctg ctc tag                                 1227
Gly Lys Pro Leu Lys Glu Leu Leu
                405

<210> SEQ ID NO 7
<211> LENGTH: 408
<212> TYPE: PRT
<213> ORGANISM: Pseudomonas maltophilia DI-6

<400> SEQUENCE: 7

Met Ser Lys Ala Asp Val Val Ile Val Gly Ala Gly His Gly Gly Ala
1               5                   10                  15

Gln Cys Ala Ile Ala Leu Arg Gln Asn Gly Phe Glu Gly Thr Ile Thr
            20                  25                  30

Val Ile Gly Arg Glu Pro Glu Tyr Pro Tyr Glu Arg Pro Pro Leu Ser
        35                  40                  45

Lys Glu Tyr Phe Ala Arg Glu Lys Thr Phe Asp Arg Leu Tyr Ile Arg
    50                  55                  60

Pro Pro Thr Phe Trp Ala Glu Lys Asn Ile Glu Phe Lys Leu Gly Thr
65                  70                  75                  80

Glu Val Thr Lys Val Asp Pro Lys Ala His Glu Leu Thr Leu Ser Asn
                85                  90                  95

Gly Glu Ser Tyr Gly Tyr Gly Lys Leu Val Trp Ala Thr Gly Gly Asp
            100                 105                 110

Pro Arg Arg Leu Ser Cys Gln Gly Ala Asp Leu Thr Gly Ile His Ala
        115                 120                 125

Val Arg Thr Arg Glu Asp Cys Asp Thr Leu Met Ala Glu Val Asp Ala
    130                 135                 140

Gly Thr Lys Asn Ile Val Ile Gly Gly Tyr Ile Gly Leu Glu
145                 150                 155                 160

Ala Ala Ala Val Leu Ser Lys Met Gly Leu Lys Val Thr Leu Leu Glu
                165                 170                 175

Ala Leu Pro Arg Val Leu Ala Arg Val Ala Gly Glu Asp Leu Ser Thr
            180                 185                 190
```

```
Phe Tyr Gln Lys Glu His Val Asp His Gly Val Asp Leu Arg Thr Glu
        195                 200                 205

Val Met Val Asp Ser Leu Val Gly Glu Asn Gly Lys Val Thr Gly Val
    210                 215                 220

Gln Leu Ala Gly Gly Glu Val Ile Pro Ala Gly Val Ile Val Gly
225                 230                 235                 240

Ile Gly Ile Val Pro Ala Val Gly Pro Leu Ile Ala Ala Gly Ala Ala
                245                 250                 255

Gly Ala Asn Gly Val Asp Val Asp Glu Tyr Cys Arg Thr Ser Leu Pro
            260                 265                 270

Asp Ile Tyr Ala Ile Gly Asp Cys Ala Ala Phe Ala Cys Asp Tyr Ala
            275                 280                 285

Gly Gly Asn Val Met Arg Val Glu Ser Val Gln Asn Ala Asn Asp Met
            290                 295                 300

Gly Thr Cys Val Ala Lys Ala Ile Cys Gly Asp Glu Lys Pro Tyr Lys
305                 310                 315                 320

Ala Phe Pro Trp Phe Trp Ser Asn Gln Tyr Asp Leu Lys Leu Gln Thr
                325                 330                 335

Ala Gly Ile Asn Leu Gly Phe Asp Lys Thr Val Ile Arg Gly Asn Pro
            340                 345                 350

Glu Glu Arg Ser Phe Ser Val Val Tyr Leu Lys Asp Gly Arg Val Val
            355                 360                 365

Ala Leu Asp Cys Val Asn Met Val Lys Asp Tyr Val Gln Gly Arg Lys
            370                 375                 380

Leu Val Glu Ala Gly Ala Thr Pro Asp Leu Glu Ala Leu Ala Asp Ala
385                 390                 395                 400

Gly Lys Pro Leu Lys Glu Leu Leu
                405

<210> SEQ ID NO 8
<211> LENGTH: 1230
<212> TYPE: DNA
<213> ORGANISM: Pseudomonas maltophilia DI-6
<220> FEATURE:
<221> NAME/KEY: CDS
<222> LOCATION: (1)..(1230)

<400> SEQUENCE: 8 atg cag agg gca gac gtc gta atc gtg gga gcc ggg cat ggc ggt gca      48
Met Gln Arg Ala Asp Val Val Ile Val Gly Ala Gly His Gly Gly Ala
1               5                   10                  15 cag tgc gcg atc gcc ctt cgc cag aac ggc ttc gaa ggc acc atc acc      96
Gln Cys Ala Ile Ala Leu Arg Gln Asn Gly Phe Glu Gly Thr Ile Thr
                20                  25                  30 gtc atc ggt cgt gag ccg gaa tat ccc tat gag cgt ccg ccg ctc tcg     144
Val Ile Gly Arg Glu Pro Glu Tyr Pro Tyr Glu Arg Pro Pro Leu Ser
            35                  40                  45 aag gaa tat ttc gcg cgc gag aag acc ttc gac cgc ctc tac atc cgt     192
Lys Glu Tyr Phe Ala Arg Glu Lys Thr Phe Asp Arg Leu Tyr Ile Arg
        50                  55                  60 ccg ccg acg ttc tgg gcc gag aag aac atc gag ttc aag ctt ggc acc     240
Pro Pro Thr Phe Trp Ala Glu Lys Asn Ile Glu Phe Lys Leu Gly Thr
65                  70                  75                  80 gaa gtc acc aag gtc gat ccc aag gcg cac gaa ctg acg ctc tcc aac     288
Glu Val Thr Lys Val Asp Pro Lys Ala His Glu Leu Thr Leu Ser Asn
                85                  90                  95 ggc gag agc tac ggt tat ggc aag ctc gtc tgg gcc acc ggc ggc gat     336
Gly Glu Ser Tyr Gly Tyr Gly Lys Leu Val Trp Ala Thr Gly Gly Asp
```

-continued

```
                100                     105                     110
ccg cgt cgc ctt tct tgc cag ggg gcc gac ctc acc ggc atc cac gcc      384
Pro Arg Arg Leu Ser Cys Gln Gly Ala Asp Leu Thr Gly Ile His Ala
        115                     120                     125 gtg cgc acc cgc gag gac tgc gac acg ctg atg gcc gaa gtc gat gcg      432
Val Arg Thr Arg Glu Asp Cys Asp Thr Leu Met Ala Glu Val Asp Ala
130                     135                     140 ggc acg aag aac atc gtc gtc atc ggc ggc tac atc ggt ctg gaa          480
Gly Thr Lys Asn Ile Val Val Ile Gly Gly Tyr Ile Gly Leu Glu
145                     150                     155                     160 gcc gct gcg gtg ctg tcc aag atg ggc ctc aag gtc acc ctc ctc gaa      528
Ala Ala Ala Val Leu Ser Lys Met Gly Leu Lys Val Thr Leu Leu Glu
                165                     170                     175 gcg ctt ccg cgc gtg ctg gcg cgc gtt gcg ggt gaa gac ctc tcg acc      576
Ala Leu Pro Arg Val Leu Ala Arg Val Ala Gly Glu Asp Leu Ser Thr
            180                     185                     190 ttc tac cag aag gaa cat gtc gat cac ggc gtc gac ctg cgc acc gaa      624
Phe Tyr Gln Lys Glu His Val Asp His Gly Val Asp Leu Arg Thr Glu
        195                     200                     205 gtc atg gtc gac agc ctc gtc ggc gaa aac ggc aag gtc acc ggc gtg      672
Val Met Val Asp Ser Leu Val Gly Glu Asn Gly Lys Val Thr Gly Val
    210                     215                     220 cag ctt gcc ggc ggc gaa gtg atc ccg gcc gaa ggc gtc atc gtc ggc      720
Gln Leu Ala Gly Gly Glu Val Ile Pro Ala Glu Gly Val Ile Val Gly
225                     230                     235                     240 atc ggc atc gtg cct gcc atc ggt ccg ctg atc gcg gcc ggc gcg gcc      768
Ile Gly Ile Val Pro Ala Ile Gly Pro Leu Ile Ala Ala Gly Ala Ala
                245                     250                     255 ggc gcc aac ggc gtc gac gtg gac gag tac tgc cgc acc tcg ctg ccc      816
Gly Ala Asn Gly Val Asp Val Asp Glu Tyr Cys Arg Thr Ser Leu Pro
            260                     265                     270 gac atc tat gcg atc ggc gac tgt gcg gct ttc gcc tgc gac tac gcc      864
Asp Ile Tyr Ala Ile Gly Asp Cys Ala Ala Phe Ala Cys Asp Tyr Ala
        275                     280                     285 ggc ggc aac gtg atg cgc gtg gaa tcg gtc cag aac gcc aac gac atg      912
Gly Gly Asn Val Met Arg Val Glu Ser Val Gln Asn Ala Asn Asp Met
    290                     295                     300 ggc acc tgc gtg gcc aag gcg atc tgc ggc gac gag aag ccc tac aag      960
Gly Thr Cys Val Ala Lys Ala Ile Cys Gly Asp Glu Lys Pro Tyr Lys
305                     310                     315                     320 gcg ttc ccg tgg ttc tgg tcc aac cag tac gac ctc aag ctg cag acc     1008
Ala Phe Pro Trp Phe Trp Ser Asn Gln Tyr Asp Leu Lys Leu Gln Thr
                325                     330                     335 gcc ggc atc aac ctg ggc ttc gac aag acc gtg atc cgc ggc aat ccg     1056
Ala Gly Ile Asn Leu Gly Phe Asp Lys Thr Val Ile Arg Gly Asn Pro
            340                     345                     350 gag gag cgc agc ttc tcg gtc gtc tat ctc aag gac ggc cgc gtg gtc     1104
Glu Glu Arg Ser Phe Ser Val Val Tyr Leu Lys Asp Gly Arg Val Val
        355                     360                     365 gcg ctg gac tgc gtg aac atg gtc aag gat tac gtg cag ggc cgc aag     1152
Ala Leu Asp Cys Val Asn Met Val Lys Asp Tyr Val Gln Gly Arg Lys
    370                     375                     380 ctg gtc gaa gcc ggg gcc acc ccc gac ctc gaa gcg ctg gcc gat gcc     1200
Leu Val Glu Ala Gly Ala Thr Pro Asp Leu Glu Ala Leu Ala Asp Ala
385                     390                     395                     400 ggc aag ccg ctc aag gaa ctg caa tac tag                             1230
Gly Lys Pro Leu Lys Glu Leu Gln Tyr
                405
```

<210> SEQ ID NO 9
<211> LENGTH: 409
<212> TYPE: PRT
<213> ORGANISM: Pseudomonas maltophilia DI-6

<400> SEQUENCE: 9

```
Met Gln Arg Ala Asp Val Val Ile Val Gly Ala Gly His Gly Gly Ala
1               5                   10                  15

Gln Cys Ala Ile Ala Leu Arg Gln Asn Gly Phe Glu Gly Thr Ile Thr
            20                  25                  30

Val Ile Gly Arg Glu Pro Glu Tyr Pro Tyr Glu Arg Pro Pro Leu Ser
        35                  40                  45

Lys Glu Tyr Phe Ala Arg Glu Lys Thr Phe Asp Arg Leu Tyr Ile Arg
    50                  55                  60

Pro Pro Thr Phe Trp Ala Glu Lys Asn Ile Glu Phe Lys Leu Gly Thr
65                  70                  75                  80

Glu Val Thr Lys Val Asp Pro Lys Ala His Glu Leu Thr Leu Ser Asn
                85                  90                  95

Gly Glu Ser Tyr Gly Tyr Gly Lys Leu Val Trp Ala Thr Gly Gly Asp
            100                 105                 110

Pro Arg Arg Leu Ser Cys Gln Gly Ala Asp Leu Thr Gly Ile His Ala
        115                 120                 125

Val Arg Thr Arg Glu Asp Cys Asp Thr Leu Met Ala Glu Val Asp Ala
    130                 135                 140

Gly Thr Lys Asn Ile Val Val Ile Gly Gly Gly Tyr Ile Gly Leu Glu
145                 150                 155                 160

Ala Ala Ala Val Leu Ser Lys Met Gly Leu Lys Val Thr Leu Leu Glu
                165                 170                 175

Ala Leu Pro Arg Val Leu Ala Arg Val Ala Gly Glu Asp Leu Ser Thr
            180                 185                 190

Phe Tyr Gln Lys Glu His Val Asp His Gly Val Asp Leu Arg Thr Glu
        195                 200                 205

Val Met Val Asp Ser Leu Val Gly Glu Asn Gly Lys Val Thr Gly Val
    210                 215                 220

Gln Leu Ala Gly Gly Glu Val Ile Pro Ala Glu Gly Val Ile Val Gly
225                 230                 235                 240

Ile Gly Ile Val Pro Ala Ile Gly Pro Leu Ile Ala Ala Gly Ala Ala
                245                 250                 255

Gly Ala Asn Gly Val Asp Val Asp Glu Tyr Cys Arg Thr Ser Leu Pro
            260                 265                 270

Asp Ile Tyr Ala Ile Gly Asp Cys Ala Ala Phe Ala Cys Asp Tyr Ala
        275                 280                 285

Gly Gly Asn Val Met Arg Val Glu Ser Val Gln Asn Ala Asn Asp Met
    290                 295                 300

Gly Thr Cys Val Ala Lys Ala Ile Cys Gly Asp Glu Lys Pro Tyr Lys
305                 310                 315                 320

Ala Phe Pro Trp Phe Trp Ser Asn Gln Tyr Asp Leu Lys Leu Gln Thr
                325                 330                 335

Ala Gly Ile Asn Leu Gly Phe Asp Lys Thr Val Ile Arg Gly Asn Pro
            340                 345                 350

Glu Glu Arg Ser Phe Ser Val Val Tyr Leu Lys Asp Gly Arg Val Val
        355                 360                 365

Ala Leu Asp Cys Val Asn Met Val Lys Asp Tyr Val Gln Gly Arg Lys
    370                 375                 380
```

```
Leu Val Glu Ala Gly Ala Thr Pro Asp Leu Glu Ala Leu Ala Asp Ala
385                 390                 395                 400

Gly Lys Pro Leu Lys Glu Leu Gln Tyr
                405

<210> SEQ ID NO 10
<211> LENGTH: 106
<212> TYPE: PRT
<213> ORGANISM: Rhodobacter capsulatus

<400> SEQUENCE: 10

Ala Lys Ile Ile Phe Ile Glu His Asn Gly Thr Arg His Glu Val Glu
1               5                   10                  15

Ala Lys Pro Gly Leu Thr Val Met Glu Ala Ala Arg Asp Asn Gly Val
                20                  25                  30

Pro Gly Ile Asp Ala Asp Cys Gly Gly Ala Cys Ala Cys Ser Thr Cys
            35                  40                  45

His Ala Tyr Val Asp Pro Ala Trp Val Asp Lys Leu Pro Lys Ala Leu
    50                  55                  60

Pro Thr Glu Thr Asp Met Ile Asp Phe Ala Tyr Glu Pro Asn Pro Ala
65                  70                  75                  80

Thr Ser Arg Leu Thr Cys Gln Ile Lys Val Thr Ser Leu Leu Asp Gly
                85                  90                  95

Leu Val Val His Leu Pro Glu Lys Gln Ile
                100                 105

<210> SEQ ID NO 11
<211> LENGTH: 106
<212> TYPE: PRT
<213> ORGANISM: Caulobacter crescentus

<400> SEQUENCE: 11

Met Ala Lys Ile Thr Tyr Ile Gln His Asp Gly Ala Glu Gln Val Ile
1               5                   10                  15

Asp Val Lys Pro Gly Leu Thr Val Met Glu Gly Ala Val Lys Asn Asn
                20                  25                  30

Val Pro Gly Ile Asp Ala Asp Cys Gly Gly Ala Cys Ala Cys Ala Thr
            35                  40                  45

Cys His Val Tyr Val Asp Glu Ala Trp Leu Asp Lys Thr Gly Asp Lys
    50                  55                  60

Ser Ala Met Glu Glu Ser Met Leu Asp Phe Ala Glu Asn Val Glu Pro
65                  70                  75                  80

Asn Ser Arg Leu Ser Cys Gln Ile Lys Val Ser Asp Ala Leu Asp Gly
                85                  90                  95

Leu Val Val Arg Leu Pro Glu Ser Gln His
                100                 105

<210> SEQ ID NO 12
<211> LENGTH: 106
<212> TYPE: PRT
<213> ORGANISM: Rhodococcus erythropolis

<400> SEQUENCE: 12

Pro Thr Val Thr Tyr Val His Pro Asp Gly Thr Lys His Glu Val Glu
1               5                   10                  15

Val Pro Thr Gly Lys Arg Val Met Gln Ala Ala Ile Gly Ala Gly Ile
                20                  25                  30

Asp Gly Ile Val Ala Glu Cys Gly Gly Gln Ala Met Cys Ala Thr Cys
```

-continued

```
                 35                  40                  45
His Val Tyr Val Glu Ser Pro Trp Ala Asp Lys Phe Pro Ser Ile Ser
     50                  55                  60

Glu Glu Glu Asp Glu Met Leu Asp Asp Thr Val Ser Pro Arg Thr Glu
 65                  70                  75                  80

Ala Ser Arg Leu Ser Cys Gln Leu Val Val Ser Asp Val Asp Gly
                 85                  90                  95

Leu Ile Val Arg Leu Pro Glu Glu Gln Val
            100                 105

<210> SEQ ID NO 13
<211> LENGTH: 106
<212> TYPE: PRT
<213> ORGANISM: Pseudomonas putida

<400> SEQUENCE: 13

Ser Lys Val Val Tyr Val Ser His Asp Gly Thr Arg Arg Glu Leu Asp
 1               5                  10                  15

Val Ala Asp Gly Val Ser Leu Met Gln Ala Ala Val Ser Asn Gly Ile
                 20                  25                  30

Tyr Asp Ile Val Gly Asp Cys Gly Gly Ser Ala Ser Cys Ala Thr Cys
             35                  40                  45

His Val Tyr Val Asn Glu Ala Phe Thr Asp Lys Val Pro Ala Ala Asn
     50                  55                  60

Glu Arg Glu Ile Gly Met Leu Glu Cys Val Thr Ala Glu Leu Lys Pro
 65                  70                  75                  80

Asn Ser Arg Leu Cys Cys Gln Ile Ile Met Thr Pro Glu Leu Asp Gly
                 85                  90                  95

Ile Val Val Asp Val Pro Asp Arg Gln Trp
            100                 105

<210> SEQ ID NO 14
<211> LENGTH: 105
<212> TYPE: PRT
<213> ORGANISM: Pseudomonas sp.

<400> SEQUENCE: 14

Pro Arg Val Val Phe Ile Asp Glu Gln Ser Gly Glu Tyr Ala Val Asp
 1               5                  10                  15

Ala Gln Asp Gly Gln Ser Leu Met Glu Val Ala Thr Gln Asn Gly Val
                 20                  25                  30

Pro Gly Ile Val Ala Glu Cys Gly Gly Ser Cys Val Cys Ala Thr Cys
             35                  40                  45

Arg Ile Glu Ile Glu Asp Ala Trp Val Glu Ile Val Gly Glu Ala Asn
     50                  55                  60

Pro Asp Glu Asn Asp Leu Leu Gln Ser Thr Gly Glu Pro Met Thr Ala
 65                  70                  75                  80

Gly Thr Arg Leu Ser Cys Gln Val Phe Ile Asp Pro Ser Met Asp Gly
                 85                  90                  95

Leu Ile Val Arg Val Pro Leu Pro Ala
            100                 105

<210> SEQ ID NO 15
<211> LENGTH: 409
<212> TYPE: PRT
<213> ORGANISM: Sphingomonas sp.

<400> SEQUENCE: 15
```

```
Met Arg Ser Ala Asp Val Val Ile Val Gly Ala Gly His Ala Gly Ala
1               5                   10                  15

Gln Cys Ala Ile Ala Leu Arg Gln Ala Gly Tyr Glu Gly Ser Ile Ala
            20                  25                  30

Leu Val Gly Arg Glu Asn Glu Val Pro Tyr Glu Arg Pro Pro Leu Ser
        35                  40                  45

Lys Glu Tyr Phe Ser Arg Glu Lys Ser Phe Glu Arg Leu Tyr Ile Arg
50                  55                  60

Pro Pro Glu Phe Trp Arg Glu Lys Asp Ile His Leu Thr Leu Gly Ile
65              70                  75                  80

Glu Val Ser Ala Val Asp Pro Gly Ser Lys Val Leu Thr Leu Ser Asp
                85                  90                  95

Gly Ser Ala Phe Ala Tyr Gly Gln Leu Val Trp Ala Thr Gly Gly Asp
                100                 105                 110

Pro Arg Lys Leu Ala Cys Pro Gly Ala Glu Leu Ser Gly Val His Ala
            115                 120                 125

Ile Arg Thr Arg Ala Asp Cys Asp Arg Leu Met Ala Glu Ile Asp Arg
130                 135                 140

Gly Leu Thr Gln Val Val Val Gly Gly Tyr Ile Gly Leu Glu
145                 150                 155                 160

Ala Ala Ala Val Leu Thr Lys Leu Asn Cys His Val Thr Leu Leu Glu
                165                 170                 175

Ala Met Pro Arg Val Leu Ala Arg Val Ala Gly Thr Glu Leu Ser Thr
            180                 185                 190

Phe Tyr Glu Asn Glu His Arg Gly His Gly Val Asp Leu Arg Thr Gly
        195                 200                 205

Ile Thr Val Ala Ala Leu Glu Gly Gln Glu Ser Val Thr Gly Val Arg
210                 215                 220

Leu Gly Asp Gly Ser Val Leu Pro Ala Gln Ala Val Ile Val Gly Ile
225                 230                 235                 240

Gly Ile Val Pro Ala Val Ala Pro Leu Ile Glu Ala Gly Ala Ala Gly
            245                 250                 255

Asp Gly Gly Val Thr Val Asp Glu Tyr Cys Arg Thr Ser Leu Pro Asp
            260                 265                 270

Val Phe Ala Ile Gly Asp Cys Ala Ser Phe Ser Cys Ser Phe Ala Asp
            275                 280                 285

Gly Arg Val Leu Arg Val Glu Ser Val Gln Asn Ala Asn Asp Gln Ala
290                 295                 300

Ser Cys Val Ala Lys Thr Ile Cys Gly Asp Pro Gln Pro Tyr Arg Ala
305                 310                 315                 320

Phe Pro Trp Phe Trp Ser Asn Gln Tyr Asp Leu Arg Leu Gln Thr Ala
                325                 330                 335

Gly Leu Ser Leu Gly Tyr Asp Gln Thr Val Val Arg Gly Asp Pro Ala
                340                 345                 350

Val Arg Ser Phe Ser Val Leu Tyr Leu Lys Gln Gly Arg Val Ile Ala
                355                 360                 365

Leu Asp Cys Val Asn Met Val Lys Asp Tyr Val Gln Gly Arg Lys Leu
370                 375                 380

Val Glu Ala Asn Val Cys Val Ser Pro Glu Gln Leu Val Asp Thr Gly
385                 390                 395                 400

Leu Ala Leu Lys Asp Leu Ile Pro Val
                405
```

```
<210> SEQ ID NO 16
<211> LENGTH: 427
<212> TYPE: PRT
<213> ORGANISM: Rhodococcus erythropolis

<400> SEQUENCE: 16

Ser Ile Val Ile Gly Ser Gly Gln Ala Gly Phe Glu Ala Ala Val
1               5                   10                  15

Ser Leu Arg Ser His Gly Phe Ser Gly Thr Ile Thr Leu Val Gly Asp
            20                  25                  30

Glu Pro Gly Val Pro Tyr Gln Arg Pro Pro Leu Ser Lys Ala Tyr Leu
            35                  40                  45

His Ser Asp Pro Asp Arg Glu Ser Leu Ala Leu Arg Pro Ala Gln Tyr
        50                  55                  60

Phe Asp Asp His Arg Ile Thr Leu Thr Cys Gly Lys Pro Val Val Arg
65                  70                  75                  80

Ile Asp Arg Asp Ala Gln Arg Val Glu Leu Ile Asp Ala Thr Ala Ile
                85                  90                  95

Glu Tyr Asp His Leu Ile Leu Ala Thr Gly Ala Arg Asn Arg Leu Leu
            100                 105                 110

Pro Val Pro Gly Ala Asn Leu Pro Gly Val His Tyr Leu Arg Thr Ala
        115                 120                 125

Gly Glu Ala Glu Ser Leu Thr Ser Ser Met Ala Ser Cys Ser Ser Leu
    130                 135                 140

Val Val Ile Gly Ala Gly Phe Ile Gly Leu Glu Val Ala Ala Ala Ala
145                 150                 155                 160

Arg Lys Lys Gly Leu Asp Val Thr Val Val Glu Ala Met Asp Arg Pro
                165                 170                 175

Met Ala Arg Ala Leu Ser Ser Val Met Ser Gly Tyr Phe Ser Thr Ala
            180                 185                 190

His Thr Glu His Gly Val His Met Arg Leu Ser Thr Gly Val Lys Thr
        195                 200                 205

Ile Asn Ala Ala Asp Gly Arg Ala Ala Gly Val Thr Thr Asn Ser Gly
    210                 215                 220

Asp Val Ile His Ala Asp Ala Val Val Gly Ile Gly Val Val Pro
225                 230                 235                 240

Asn Ile Glu Leu Ala Ala Leu Thr Gly Leu Pro Val Asp Asn Gly Ile
                245                 250                 255

Val Val Asp Glu Tyr Leu Arg Thr Pro Asp Glu Asn Ile Ser Ala Ile
            260                 265                 270

Gly Asp Cys Ala Ala Tyr Pro Ile Pro Gly Lys Ala Gly Leu Val Arg
        275                 280                 285

Leu Glu Ser Val Gln Asn Ala Val Asp Gln Ala Arg Cys Leu Ala Ala
    290                 295                 300

Gln Leu Thr Gly Thr Ser Thr His Tyr Arg Ser Val Pro Trp Phe Trp
305                 310                 315                 320

Ser Glu Gln Tyr Glu Ser Lys Leu Gln Met Ala Gly Leu Thr Ala Gly
                325                 330                 335

Ala Asp Thr His Val Val Arg Gly Ser Val Asp Ser Gly Val Phe Ser
            340                 345                 350

Ile Phe Cys Phe Leu Gly Thr Arg Leu Leu Gly Val Glu Ser Val Asn
        355                 360                 365

Lys Pro Arg Asp His Met Ala Ala Arg Lys Ile Leu Ala Thr Glu Met
    370                 375                 380
```

-continued

```
Pro Leu Thr Pro Glu Gln Ala Ala Asp Thr Asp Phe Asp Leu Lys Leu
385                 390                 395                 400

Ala Ile Ala Arg His Lys Asp Thr His Glu Lys Asp Glu Val Ala Ser
            405                 410                 415

Ala Asp Ile Gly Glu Arg Gln Val Val Ala Ser
        420                 425
```

<210> SEQ ID NO 17
<211> LENGTH: 422
<212> TYPE: PRT
<213> ORGANISM: Pseudomonas putida

<400> SEQUENCE: 17

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45

Ser Lys Ala Tyr Leu Ala Gly Lys Ala Thr Ala Glu Ser Leu Tyr Leu
50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Gln Val Ile Leu Ser
            85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
            165                 170                 175

Leu Leu Asp Thr Ala Ala Arg Val Leu Glu Arg Val Thr Ala Pro Pro
        180                 185                 190

Val Ser Ala Phe Tyr Glu His Leu His Arg Glu Ala Gly Val Asp Ile
        195                 200                 205

Arg Thr Gly Thr Gln Val Cys Gly Phe Glu Met Ser Thr Asp Gln Gln
    210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
            245                 250                 255

Ala Ala Gly Leu Gln Val Asp Asn Gly Ile Val Ile Asn Glu His Met
        260                 265                 270

Gln Thr Ser Asp Pro Leu Ile Met Ala Val Gly Asp Cys Ala Arg Phe
    275                 280                 285

His Ser Gln Leu Tyr Asp Arg Trp Val Arg Ile Glu Ser Val Pro Asn
290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
```

```
                325                 330                 335
Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
            355                 360                 365

Asp Arg Val Leu Ala Val Asp Thr Val Asn Arg Pro Val Glu Phe Asn
            370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
            405                 410                 415

Ala Glu Leu Ser Ser Ala
            420

<210> SEQ ID NO 18
<211> LENGTH: 409
<212> TYPE: PRT
<213> ORGANISM: Pseudomonas sp.

<400> SEQUENCE: 18

Met Gly Glu Arg Arg Asp Thr Thr Val Ile Val Gly Ala Gly His Ala
1               5                   10                  15

Gly Thr Ala Ala Ala Phe Phe Leu Arg Glu Phe Gly Tyr His Gly Arg
            20                  25                  30

Val Leu Leu Leu Ser Ala Glu Thr Gln His Pro Tyr Gln Arg Pro Pro
        35                  40                  45

Leu Ser Lys Glu Tyr Leu Leu Ala Gln His Ser Thr Pro Ser Leu Leu
    50                  55                  60

Lys Gly Lys Asp Ser Tyr Ala Arg Ala Asp Ile Glu Leu Cys Leu Gln
65                  70                  75                  80

Asp Asp Val Leu Ser Ile Thr Pro Ala Ser Arg Gln Val Lys Ser Ser
                85                  90                  95

Gln Gly Ser Tyr Thr Tyr Asp His Leu Ile Leu Ala Thr Gly Ser His
            100                 105                 110

Pro Arg Phe Met Ala Thr Leu Gly Gln Ala Asp Asn Leu Cys Tyr Leu
        115                 120                 125

Ser Asp Trp Asp Asp Ala Gly Arg Ile Arg Gln Gln Leu Gly Glu Ala
    130                 135                 140

Ser Arg Ile Val Val Leu Gly Gly Gly Phe Ile Gly Leu Glu Ile Ala
145                 150                 155                 160

Ser Ser Ala Cys Lys Met Gly Lys His Val Thr Val Ile Glu Arg Ala
                165                 170                 175

Pro Arg Leu Leu Ser Arg Val Val Ser Glu Ala Phe Ala Thr Phe Ile
            180                 185                 190

Gly Asp Ile His Leu Gly Asn Gly Ile Glu Leu Arg Leu Gly Glu Glu
        195                 200                 205

Val Arg Glu Val Arg Arg Cys Thr Ser Gly Val Arg Val Asp Ala Val
    210                 215                 220

Phe Leu Ser Asp Gly Gln Leu Leu Glu Cys Asp Met Leu Val Ile Gly
225                 230                 235                 240

Val Gly Ser Glu Pro Arg Met Glu Leu Ala Thr Ala Ala Gly Leu Ala
                245                 250                 255

Cys Ala Ser Gly Val Leu Val Asp Glu His Cys His Thr Ser Asp Pro
            260                 265                 270
```

```
                        -continued
Phe Ile Ser Ala Ile Gly Asp Cys Val Ala Val Cys Pro Ser Pro Gly
        275                 280                 285

His Gln Leu Pro Arg Arg Glu Ser Val Gln Asn Ala Thr Glu Gln Ala
        290                 295                 300

Arg Leu Val Ala Ala Arg Leu Ser Gly Arg Pro Val Pro Pro Val Gln
305                 310                 315                 320

Thr Pro Trp Phe Trp Ser Asp Gln Leu Gln Ala Arg Ile Asn Leu Ala
                325                 330                 335

Gly Glu Arg Pro Ala Gln Gly Gln Val Ile Val Arg Arg Tyr Gly Gly
                340                 345                 350

Asp Lys Val Ser Met Leu Tyr Leu Gln Asp Gln Gln Leu Val Ala Ile
        355                 360                 365

Glu Ala Cys Asn Met Pro Gly Asp Cys Leu Leu Ala Arg Arg Ala Ile
        370                 375                 380

Gly Gln Asn His Ser Leu Asp Leu Ala Arg Leu Val Asp Ala Asp Val
385                 390                 395                 400

Pro Leu Lys Asp Ala Leu His Phe Ala
                405
```